United States Patent
Sato

(10) Patent No.: US 10,349,858 B2
(45) Date of Patent: Jul. 16, 2019

(54) HEARTBEAT DETECTING DEVICE AND BIOLOGICAL SIGNAL PROCESSING DEVICE

(71) Applicants: KYUSHU INSTITUTE OF TECHNOLOGY, Kitakyushu-shi, Fukuoka (JP); AI TECHNOLOGY INC., Fukuoka-shi, Fukuoka (JP)

(72) Inventor: Yasushi Sato, Kitakyushu (JP)

(73) Assignees: KYUSHU INSTITUTE OF TECHNOLOGY, Kitakyushu-shi (JP); AI TECHNOLOGY INC., Fukuoka-shi (JP)

( * ) Notice: Subject to any disclaimer, the term of this patent is extended or adjusted under 35 U.S.C. 154(b) by 155 days.

(21) Appl. No.: 15/560,756

(22) PCT Filed: Mar. 17, 2016

(86) PCT No.: PCT/JP2016/058605
§ 371 (c)(1),
(2) Date: Sep. 22, 2017

(87) PCT Pub. No.: WO2016/152743
PCT Pub. Date: Sep. 29, 2016

(65) Prior Publication Data
US 2018/0049660 A1 Feb. 22, 2018

(30) Foreign Application Priority Data
Mar. 23, 2015 (JP) .................. 2015-059284

(51) Int. Cl.
| A61B 5/00 | (2006.01) |
| A61B 5/0456 | (2006.01) |
| A61B 5/024 | (2006.01) |
| A61B 5/0245 | (2006.01) |
| A61B 5/021 | (2006.01) |
| A61B 5/0205 | (2006.01) |
| A61B 5/0452 | (2006.01) |
| A61B 5/18 | (2006.01) |

(52) U.S. Cl.
CPC ............ *A61B 5/0456* (2013.01); *A61B 5/021* (2013.01); *A61B 5/0245* (2013.01); *A61B 5/02438* (2013.01); *A61B 5/02444* (2013.01); *A61B 5/6816* (2013.01); *A61B 5/7203* (2013.01); *A61B 5/0205* (2013.01); *A61B 5/02108* (2013.01); *A61B 5/02141* (2013.01); *A61B 5/04525* (2013.01); *A61B 5/18* (2013.01); *A61B 5/6893* (2013.01); *A61B 5/7225* (2013.01); *A61B 2562/0204* (2013.01)

(58) Field of Classification Search
CPC .............................. A61B 5/0456; A61B 5/021
USPC ......................................................... 600/509
See application file for complete search history.

(56) References Cited

FOREIGN PATENT DOCUMENTS

| JP | S52-105687 A | 9/1977 |
| JP | S56-145836 A | 11/1981 |
| JP | S63-059929 A | 3/1988 |
| JP | 2012-016450 A | 1/2012 |
| WO | 2014/084162 A1 | 6/2014 |

OTHER PUBLICATIONS

May 31, 2016 Search Report issued in International Patent Application No. PCT/JP2016/058605.

*Primary Examiner* — Nadia A Mahmood
(74) *Attorney, Agent, or Firm* — Oliff PLC

(57) ABSTRACT

The difference between the current value and the last value of an RR interval is compared with a predetermined reference differential value, and an attenuation time constant of a peak-hold section is controlled according to the comparison result.

3 Claims, 14 Drawing Sheets

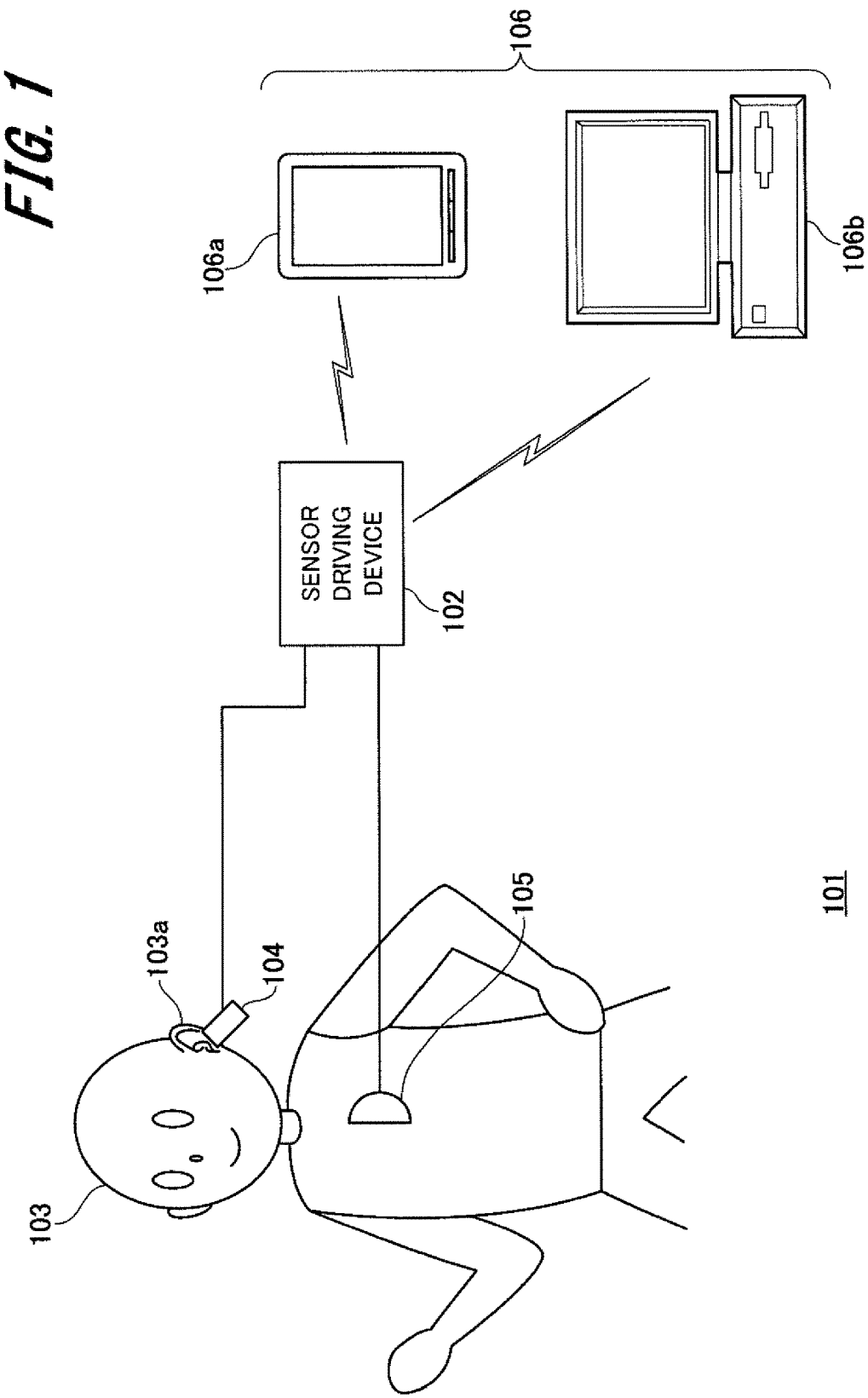

US 10,349,858 B2

HEARTBEAT DETECTING DEVICE AND BIOLOGICAL SIGNAL PROCESSING DEVICE

TECHNICAL FIELD

The present invention relates to a heartbeat detecting device adapted to detect a heartbeat signal having periodicity, and a biological signal processing device adapted to remove noise from a biological signal.

BACKGROUND ART

A heart sound, which results from the movement of a heart, includes high-frequency components caused by blood pressure. It is known that the heart sound has strong correlation with the blood pressure, and it is possible to estimate the blood pressure by suitably processing heart sound data using a computer.

Patent document 1 discloses the technical content of a central blood pressure measuring device that measures the central blood pressure based on the heart sound.

Patent document 2 discloses the content of a technique for removing noise components while detecting the heartbeat.

CITATION LIST

Patent Literature

Patent document 1: Japanese Unexamined Patent Application Publication No. 2012-16450
Patent document 2: WO2014/084162

SUMMARY OF INVENTION

Technical Problem

In the central blood pressure measuring device disclosed in Patent document 1, an acceleration sensor is used to collect the heart sound. Since the acceleration sensor is expensive, it is preferred that a general microphone (such as an electret condenser microphone, a dynamic microphone, a ceramic microphone or the like) is used, if possible, to reduce the cost of the device. However, if the aforesaid general microphone is used, noise caused by the clothes, the skin, the muscles, the bones and the like of a subject will also be collected at the same time.

In recent years, a wearable sensor possible to be constantly worn by a subject attracts a lot of attention in the market; however, in order to make the blood pressure measuring device as a wearable sensor, low price, small size, and low power consumption are preconditions. Thus, in order to make the blood pressure measuring device as a wearable sensor, it is essential to employ a technique in which a low-priced microphone is used, yet the noise can be effectively removed.

Further, if a radio wave can be used instead of a heartbeat sensor or an electrocardiogram detector, it will be possible to continuously detect the heartbeat in a non-contact manner.

The present invention is made to solve the aforesaid problems, and it is an object of the present invention to provide a heartbeat detecting device adapted to detect a heartbeat signal having periodicity, and a biological signal processing device adapted to remove noise from a biological signal.

Solution to Problem

In order to solve the aforesaid problems, a heartbeat detecting device according to an aspect of the present invention includes: a peak-hold section that holds the peak of a heartbeat signal; a first adder that outputs a difference signal between an output signal of the peak-hold section and the heartbeat signal; a first comparator that compares the output signal of the first adder with a predetermined reference signal level value; a cycle measuring section that measures the cycle of the output signal of the first comparator; and a second adder that outputs the difference between the cycle measurement outputted by the cycle measuring section and the cycle measurement outputted last time by the cycle measuring section. The heartbeat detecting device further includes: a second comparator that compares the value outputted by the second adder with a predetermined reference differential value; and a time constant controller that controls an attenuation time constant of the peak-hold section according to a logical value of the second comparator.

Advantageous Effects of Invention

According to the present invention, it is possible to provide a heartbeat detecting device adapted to detect a heartbeat signal having periodicity, and a biological signal processing device adapted to remove noise from a biological signal.

Other problems, configurations and effects than those described above will be made clear by the following description of each embodiment.

BRIEF DESCRIPTION OF DRAWINGS

FIG. 1 is a schematic view showing an overall configuration of a blood pressure measuring system;

DESCRIPTION OF EMBODIMENTS

Figure 2A:
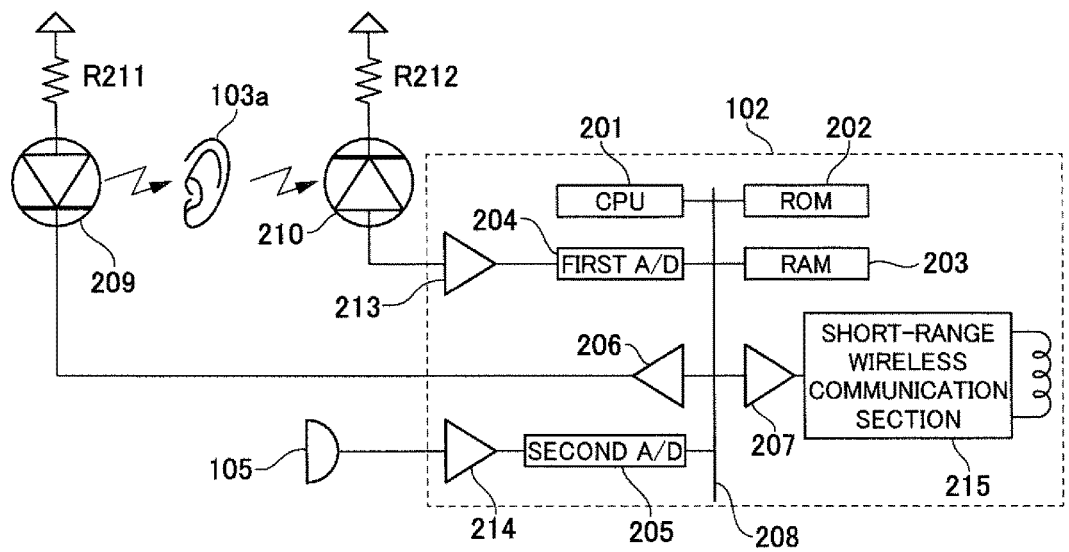
FIG. 2A and FIG. 2B are a block diagram showing a hardware configuration of a sensor driving device and a block diagram showing a hardware configuration of an information processing device.

In the following embodiment, a signal noise removing device, which constitutes a blood pressure measuring device, will be described first, and a biological signal detecting device will be described thereafter.

The signal noise removing device is an improved modification based on the art disclosed in Patent document 2.

In the signal noise removing device of the present embodiment, an orthogonal transformation and an orthogonal inverse transformation having strong noise filtering function are used in order to remove the noise mixed into a heart sound.

As widely known, an orthogonal transformation includes multiplication processing of a periodic signal. By performing the multiplication processing, frequency components other than a specific frequency are remarkably attenuated. Such feature is extremely useful as a noise filter.

A heart sound includes a blood flow sound. The blood flow sound is caused by the friction between blood and the inner walls of blood vessels when the blood flows in the blood vessels. Accordingly, the heart sound has strong correlation with the heartbeat cycle (i.e., the heart sound is a frequency component whose frequency is an integral multiple of the frequency of the heartbeat cycle).

Thus, if it is possible to only extract frequency components having strong correlation with the heartbeat cycle, it will be possible to remove the noise not associated with the heartbeat cycle.

However, since the heartbeat cycle includes fluctuations peculiar to living bodies, the heartbeat cycle is subtly not constant.

Thus, the heartbeat is separately detected by a pulse sensor, the peak of the heartbeat is detected to calculate the average value of the heartbeat cycle, and the signal waveform of the heart sound synchronous with the heartbeat is forcibly fitted to the average cycle of the heartbeat (i.e., resample). The noise components can be removed from the heart sound by performing an orthogonal transformation and then an orthogonal inverse transformation after the signal waveform of the heart sound has been forcibly fitted to the average cycle of the heartbeat.

After having performed the orthogonal inverse transformation, the waveform extracted by the orthogonal inverse transformation is restored to the original heartbeat cycle based on addresses in the buffer stored when detecting the peak of the heartbeat. By performing the above processing, the noise can be removed from the heart sound.

Further, Patent document 1 discloses a technique in which the blood pressure is estimated by using a correlation between the amplitude of the heart sound and the blood pressure.

If the signal of the noise-removed heart sound outputted by the aforesaid signal noise removing device is inputted as it is to a blood pressure measuring device disclosed in Patent document 1, it will be possible to achieve a blood pressure measuring device using a microphone.

Further, it is also possible to directly estimate the blood pressure from the orthogonal transformation of the signal noise removing device by using a correlation between the frequency components of the heart sound and the blood pressure.

In the biological signal detecting device, a radio wave, instead of a heartbeat sensor or an electrocardiogram detector, is used to detect a biological signal in a non-contact manner. The impedance of the human body varies in response to his (or her) heartbeat. Thus, variation in impedance of a human body is detected when a radio wave is passed through the human body. However, while the radio wave is being passed through the human body, the propagation state of the radio wave will largely fluctuate if the human body moves even slightly. To solve such a problem, two receiving modules are provided to cancel out the fluctuation component by using synchronous detection and differential amplification.

First Embodiment: Overall Configuration of a Blood Pressure Measuring System

FIG. 1 is a schematic view showing an overall configuration of a blood pressure measuring system 101.

A heartbeat sensor 104 attached to an outer ear 103a of a subject 103 and a heart sound microphone 105 attached to the chest of the subject 103 are connected to a sensor driving device 102. The sensor driving device 102 detects a heartbeat signal from the heartbeat sensor 104, detects a heart sound signal from the heart sound microphone 105, and performs data communication with an information processing device 106 by using a short-range wireless communication means, such as Bluetooth (registered trademark) or the like; wherein examples of the information processing device 106 include a mobile wireless terminal 106a (such as a smartphone), a personal computer 106b, and the like. Further, the sensor driving device 102 calculates the blood pressure from the heart sound, and displays the calculated blood pressure on a display of the information processing device 106. The details about the data communication will be described later with reference to FIG. 3A and FIG. 3B.

First Embodiment: Hardware Configurations of Sensor Driving Device 102 and Information Processing Device 106

FIG. 2A is a block diagram showing a hardware configuration of the sensor driving device 102.

In the sensor driving device 102 (which includes a microcomputer), a CPU 201, a ROM 202, a RAM 203, a first A/D converter 204, a second A/D converter 205, a first buffer 206 and a second buffer 207 are connected to a bus 208, wherein the first buffer 206 and the second buffer 207 constitute a serial port.

The heartbeat sensor 104 is configured by a combination of a green LED 209 and a photodiode 210, for example. A power source voltage is applied to the anode of the LED 209 through a resistor 211. The power source voltage is also applied to the cathode of the photodiode 210 through a resistor 212.

The cathode of the LED 209 is connected to the first buffer 206. The first buffer 206 (which is a widely known CMOS inverter) functions as a switch that is ON/OFF controlled through the bus 208 to thereby control the connection between the cathode of the LED 209 and a ground node. The first A/D converter 204 is connected to the anode of the photodiode 210 through a first operational amplifier 213 to convert the variation of the blood flow in the outer ear 103a of the subject into digital data, wherein the first operational amplifier 213 is adapted to perform current-voltage conversion and voltage amplification.

The second A/D converter 205 is connected to the heart sound microphone 105 through a second operational amplifier 214 to convert the heart sound detected from the chest of the subject into digital data, wherein the second operational amplifier 214 is adapted to perform voltage amplification.

A short-range wireless communication section 215 is connected to the second buffer 207 to transmit the data outputted by the sensor driving device 102 to the information processing device 106 (see FIG. 1).

Figure 2B:
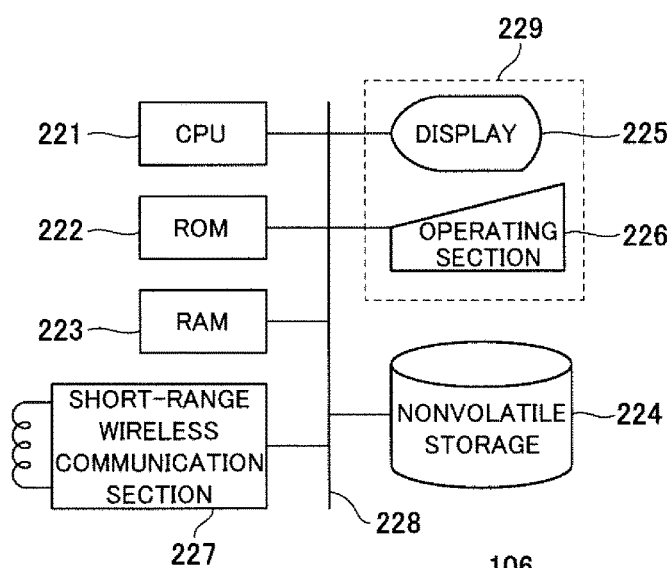

FIG. 2B is a block diagram showing a hardware configuration of the information processing device 106.

The information processing device 106 includes a CPU 221, a ROM 222, a RAM 223, a nonvolatile storage 224, a display 225, an operating section 226, and a short-range wireless communication section 227; and all these components are connected to a bus 228.

Here, in the case where the information processing device 106 is a mobile wireless terminal 106a (such as a smartphone or the like), the display 225 will be a liquid crystal display, and the operating section 226 will be a capacitance type position detecting device. The display 225 and the operating section 226 are superimposed on each other to form a touch panel display 229.

First Embodiment: Software Functions of Sensor Driving Device 102 and Information Processing Device 106

Figure 3A:
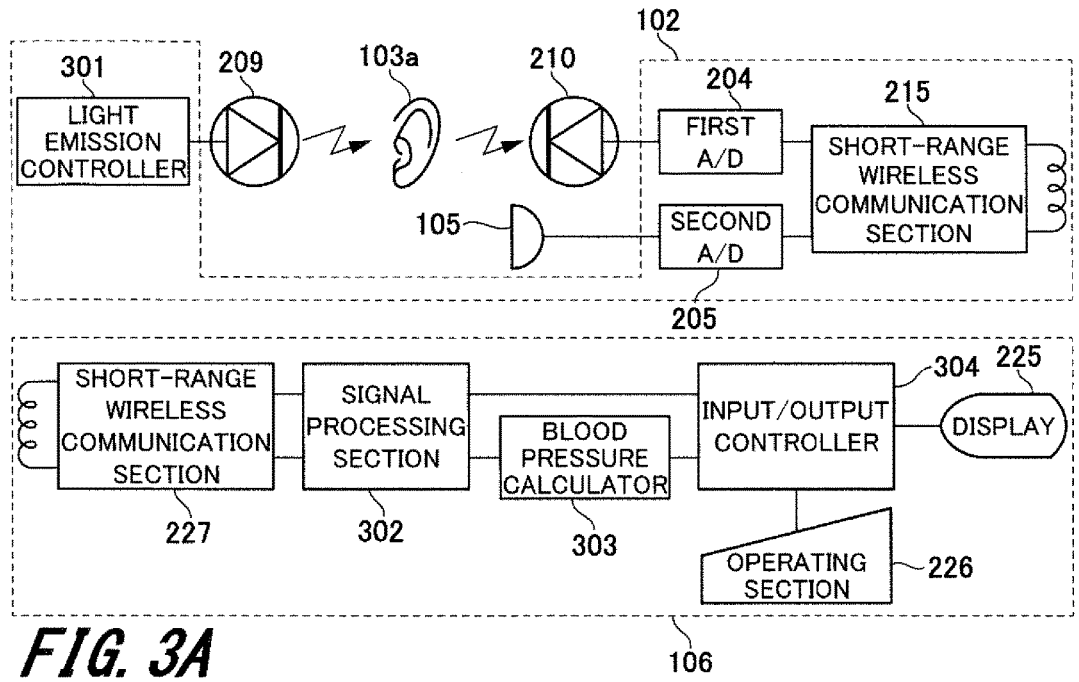
FIG. 3A and FIG. 3B are block diagrams showing software functions of the blood pressure measuring system in both cases: one is the case where arithmetic processing for measuring blood pressure is executed by the information processing device, and the other is the case where arithmetic processing for measuring blood pressure is executed by the sensor driving device.
Figure 3B:
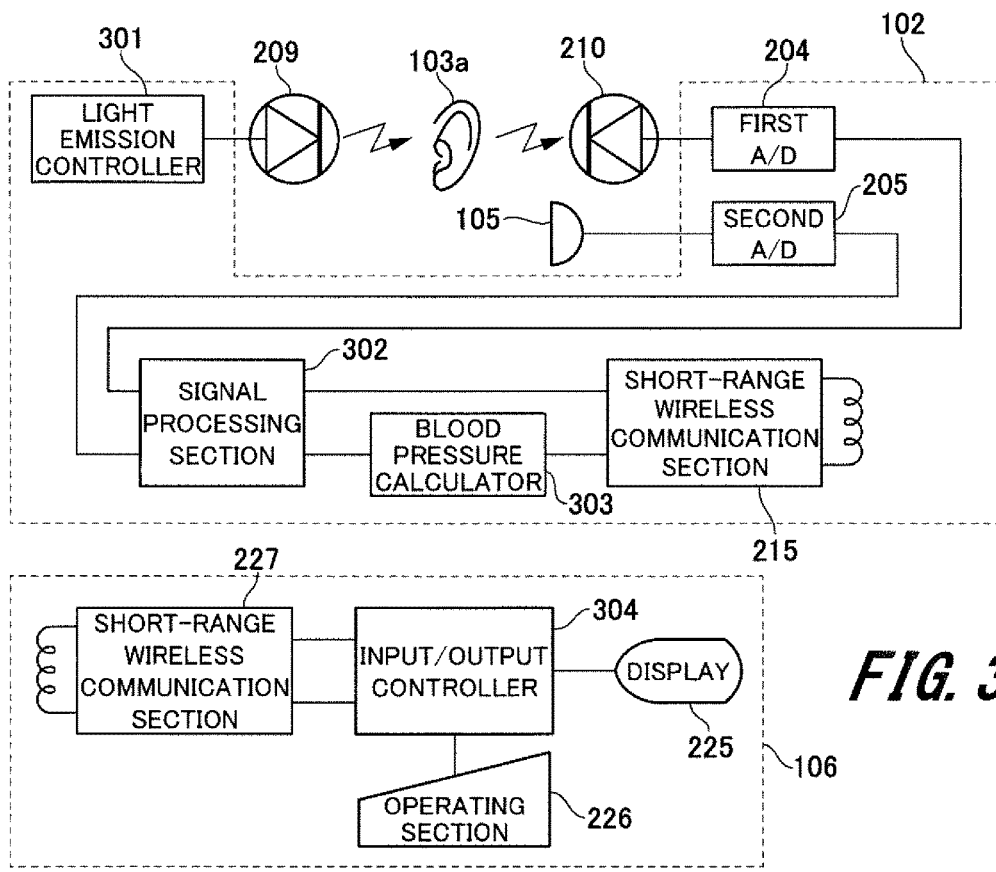

FIG. 3A and FIG. 3B are block diagrams each showing software functions of the blood pressure measuring system 101; wherein FIG. 3A shows an example in which arithmetic processing for measuring blood pressure is executed by the information processing device 106, and FIG. 3B shows an example in which arithmetic processing for measuring blood pressure is executed by the sensor driving device 102.

In the example shown in FIG. 3A, the LED 209 is driven to intermittently emit light by a light emission controller 301 of the sensor driving device 102. The light emitted by the LED 209 is transmitted though the outer ear 103a of the subject 103, and the transmitted light is detected by the photodiode 210, and converted into heartbeat data by the first A/D converter 204.

The heart sound of the subject is detected from his (or her) chest by the heart sound microphone 105, and converted into heart sound data by the second A/D converter 205.

The heartbeat data and the heart sound data are transmitted to the information processing device 106 by the short-range wireless communication section 215 of the sensor driving device 102.

The information processing device 106 receives the heartbeat data and the heart sound data from the sensor driving device 102 through the short-range wireless communication section 227. The heartbeat pulse and the heart sound data with the noise removed (hereinafter referred to as "noise-removed heart sound data") are outputted by a signal processing section 302 of the information processing device 106. A blood pressure calculator 303 analyzes the noise-removed heart sound data obtained from the signal processing section 302, and outputs blood pressure data. The heartbeat pulse and the blood pressure data are inputted to an input/output controller 304, and displayed on the display 225 as a heartbeat value and a blood pressure value.

In the example shown in FIG. 3B, the LED 209 is also driven to intermittently emit light by the light emission controller 301 of the sensor driving device 102. The light emitted by the LED 209 is transmitted though the outer ear 103a of the subject 103, the transmitted light is detected by the photodiode 210, and the detected light is converted into heartbeat data by the first A/D converter 204.

The heart sound of the subject is detected from his (or her) chest by the heart sound microphone 105, and converted into heart sound data by the second A/D converter 205.

The signal processing section 302 receives the heartbeat data and the heart sound data, and outputs the heartbeat pulse and the noise-removed heart sound data. The blood pressure calculator 303 analyzes the noise-removed heart sound data, and outputs the blood pressure data. The heartbeat pulse and the blood pressure data are transmitted to the information processing device 106 by the short-range wireless communication section 227 of the sensor driving device 102.

The information processing device 106 receives the heartbeat pulse and the blood pressure data from the sensor driving device 102 through the short-range wireless communication section 227. The heartbeat pulse and the blood pressure data are inputted to the input/output controller 304, and displayed on the display 225 as the heartbeat value and the blood pressure value.

In other words, the function of the signal processing section 302 and blood pressure calculator 303 may be provided both on the side of the information processing device 106 and on the side of the sensor driving device 102.

The signal processing section 302 may also be called as a "biological signal processing device" that removes the noise from the heart sound data based on the heartbeat data and the heart sound data.

First Embodiment: Software Functions of Signal Processing Section 302

Figure 4:
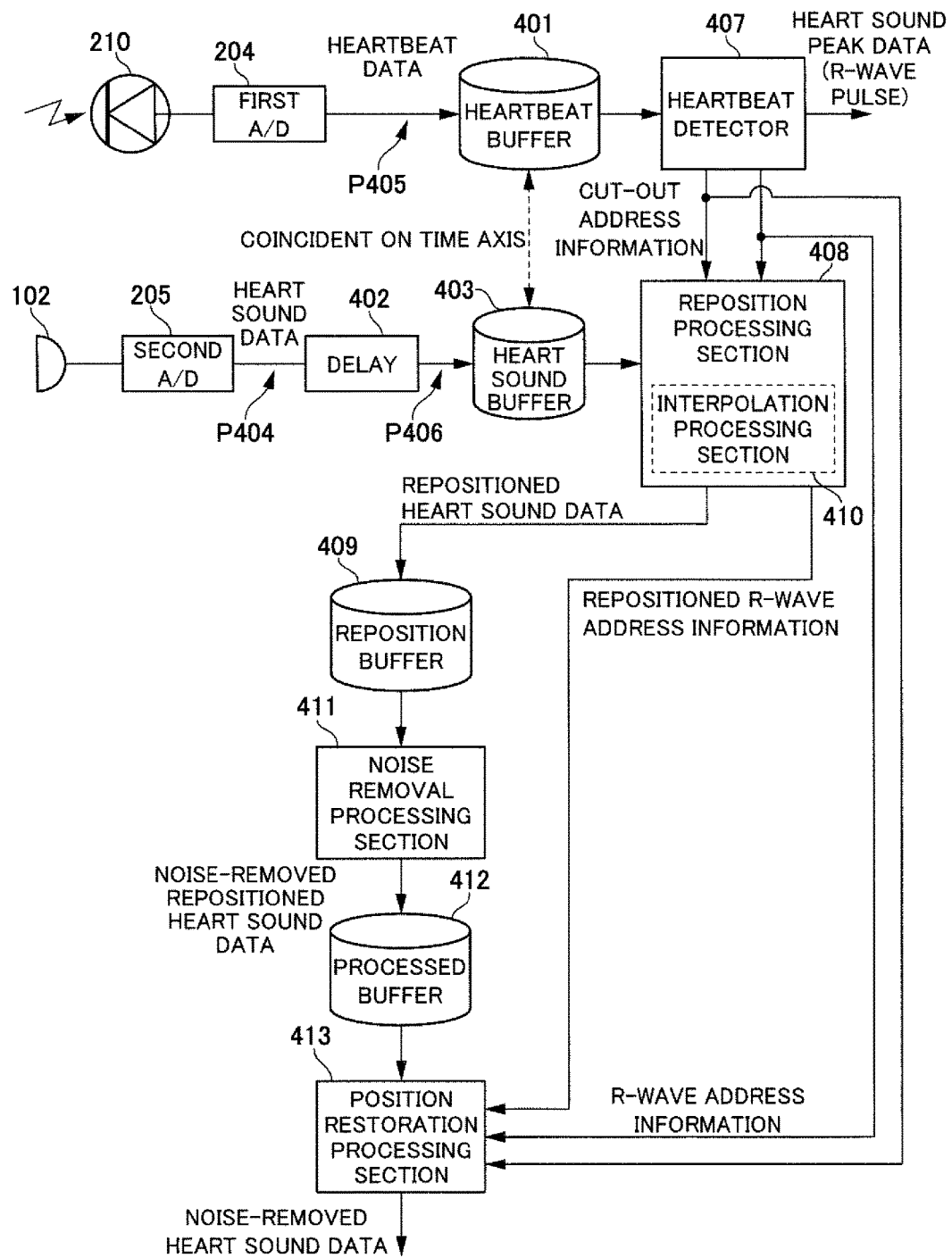
FIG. 4 is a block diagram showing software functions of a signal processing section.

FIG. 4 is a block diagrams showing software functions of the signal processing section 302.

Figure 5A:
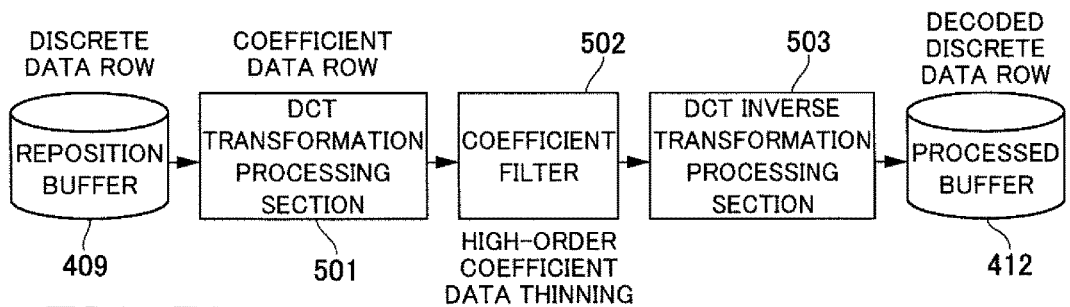
FIG. 5A, FIG. 5B and FIG. 5C are block diagrams of software functions showing an example of a noise removal processing section.
Figure 5B:
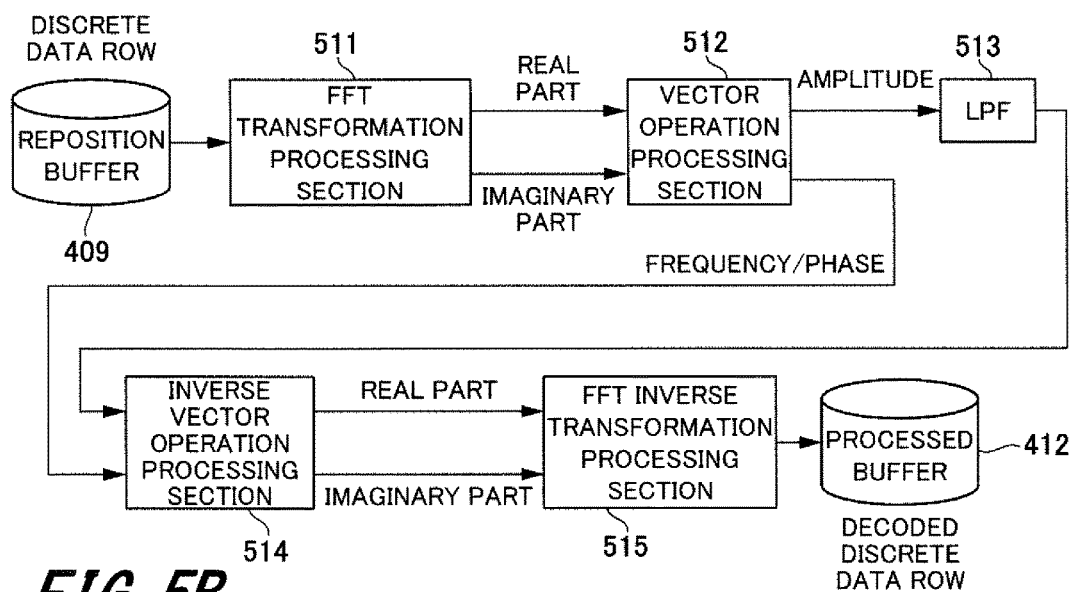

FIG. 5A and FIG. 5B are block diagrams of software functions showing an example of a noise removal processing section 411.

The heartbeat signal outputted by the photodiode 210 (which constitutes the heartbeat sensor 104) is converted into the heartbeat data by the first A/D converter 204, and stored in the heartbeat buffer 401. On the other hand, the heart sound signal outputted by the heart sound microphone 105 is converted into the heart sound data by the second A/D converter 205, and stored in a heart sound buffer 403 through a delay 402. The first A/D converter 204 and the second A/D converter 205 are configured so that the sample frequency of the first A/D converter 204 is equal to the sample frequency of the second A/D converter 205, and the heartbeat buffer 401 and the heart sound buffer 403 are configured so that the number of stored samples of the heartbeat buffer 401 is equal to the number of stored samples of the heart sound buffer 403.

The functions of the heartbeat buffer 401, the heart sound buffer 403 and the delay 402 will be described below with reference to FIG. 6.

Figure 6:
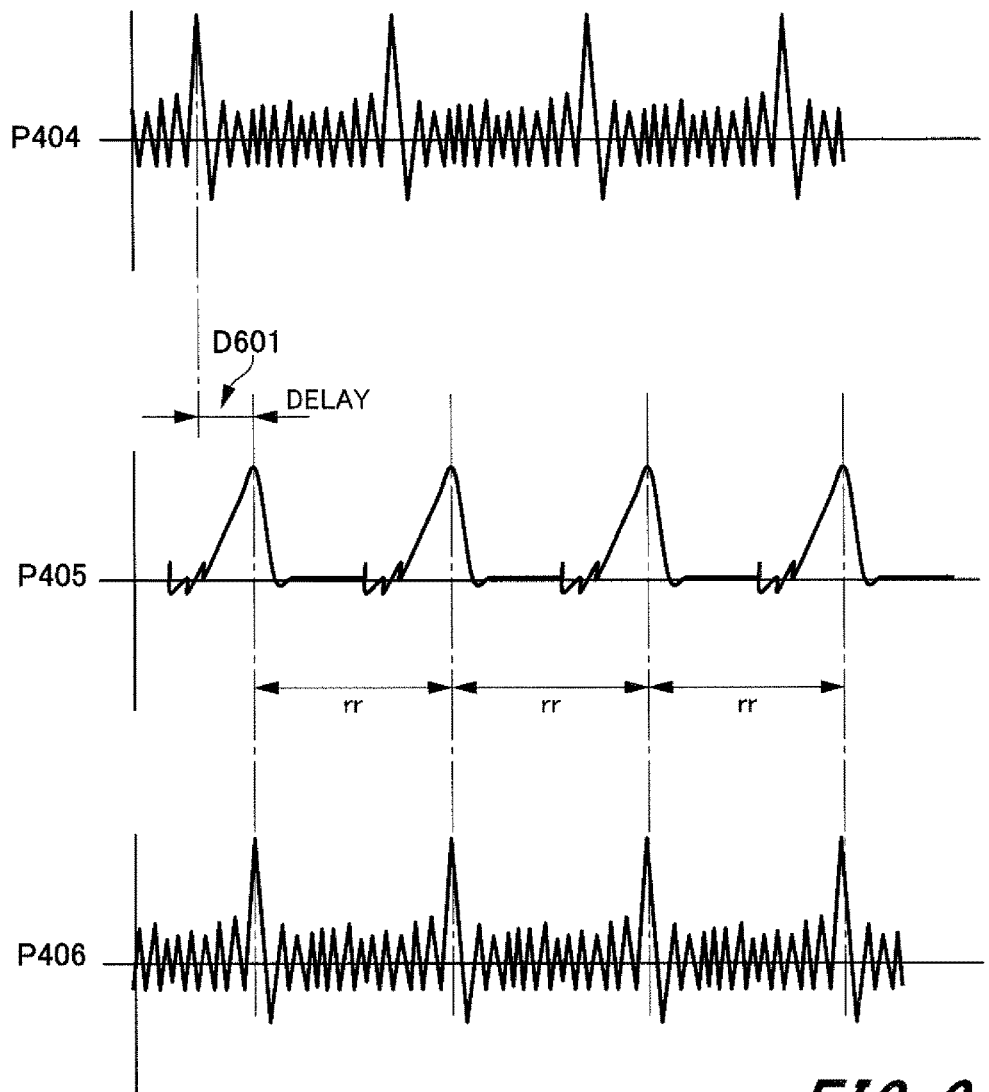
FIG. 6 shows a waveform diagram of heartbeat data, a waveform diagram of heart sound data, and a waveform diagram of heart sound data delayed by a delay.

FIG. 6 shows a waveform diagram of heartbeat data, a waveform diagram of heart sound data, and a waveform diagram of heart sound data delayed by a delay.

In the three waveforms shown in FIG. 6, the top one represents a waveform diagram of the heart sound data at detection point P404 of FIG. 4, the middle one represents a waveform diagram of the heartbeat data at detection point P405 of FIG. 4, and the bottom one represents a waveform diagram of the heart sound data delayed by the delay 402 at detection point P406 of FIG. 4.

There is a delay D601 on the time axis existing between the heart sound generated near the heart of the human body and the heartbeat detected from the outer ear 103a, the delay D601 being based on the distance between the heart and the outer ear 103a. The delay 402 cancels out the delay D601, so that the phase of the heartbeat data stored in the heartbeat buffer 401 and the phase of the heart sound data stored in the heart sound buffer 403 coincide with each other on the time axis.

Now back to the description of the signal processing section 302 again with reference to FIG. 4.

Address information of the peak of the heartbeat and address information of the range of the heartbeat are detected from the heartbeat data within the heartbeat buffer 401 by a heartbeat detector 407.

Here, the address information to be detected by the heartbeat detector 407 will be explained below by comparing the heartbeat data with the heart sound data with reference to FIG. 7.

Figure 7:
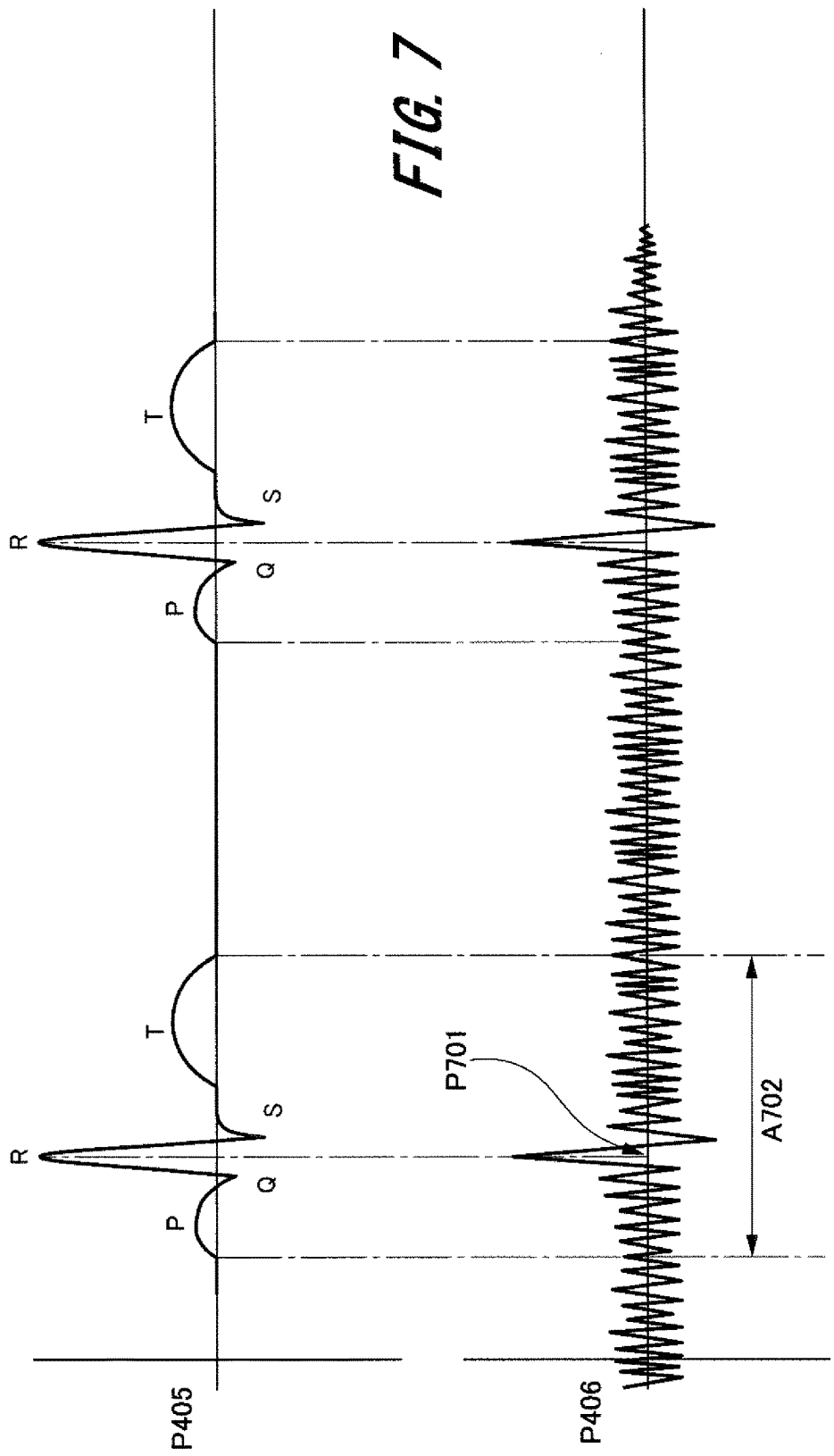
FIG. 7 shows a waveform diagram of heartbeat data and a waveform diagram of heart sound data.

FIG. 7 shows a waveform diagram of the heartbeat data stored in the heartbeat buffer 401 and a waveform diagram of the heart sound data stored in the heart sound buffer 403. The two waveform diagrams shown in FIG. 7 are equivalent to enlarged middle waveform diagram and enlarged bottom waveform diagram shown in FIG. 6.

Based on the heartbeat data stored in the heartbeat buffer 401, the heartbeat detector 407 outputs R-wave address information P701 and cut-out address information A702.

Generally, the heartbeat waveform of a healthy person includes a P-wave, a Q-wave, an R-wave, an S-wave, and a T-wave, and appearance order of these waves never changes.

First, in order to remove a DC offset component from the heartbeat data in the heartbeat buffer 401, the heartbeat detector 407 calculates a virtual zero potential by performing arithmetic processing. Further, the heartbeat detector 407 detects the address of the peak of the R-wave in the heartbeat buffer 401. The detected address of the peak of the R-wave is the R-wave address information P701.

Next, based on the virtual zero potential, the heartbeat detector 407 detects the address of the start of the P-wave and the address of the end of the T-wave, the both addresses existing before and after the R-wave address information P701. The address of the start of the P-wave and the address of the end of the T-wave represent the cut-out address information A702.

When the R-wave address information P701 in the heartbeat buffer 401 is acquired, the interval between heartbeats (i.e., RR interval) can be obtained.

Incidentally, in addition to acquiring the R-wave address information P701, the heartbeat detector 407 also outputs the heartbeat pulse. The heartbeat pulse is supplied to the input/output controller 304 (see FIG. 3A and FIG. 3B), and the input/output controller 304 measures the heartbeat value from the interval of the heartbeat pulse.

Now back to the description of the signal processing section 302 again with reference to FIG. 4.

Based on the R-wave address information P701 and the cut-out R-wave address information A702 obtained from the heartbeat detector 407, a reposition processing section 408 performs reposition processing on the heart sound data in the heart sound buffer 403. The data having been subjected to the reposition processing is outputted to and stored in a reposition buffer 409 as repositioned heart sound data.

Here, the reposition processing of the reposition processing section 408 will be explained below using the heartbeat data with reference to FIG. 8.

Figure 8:
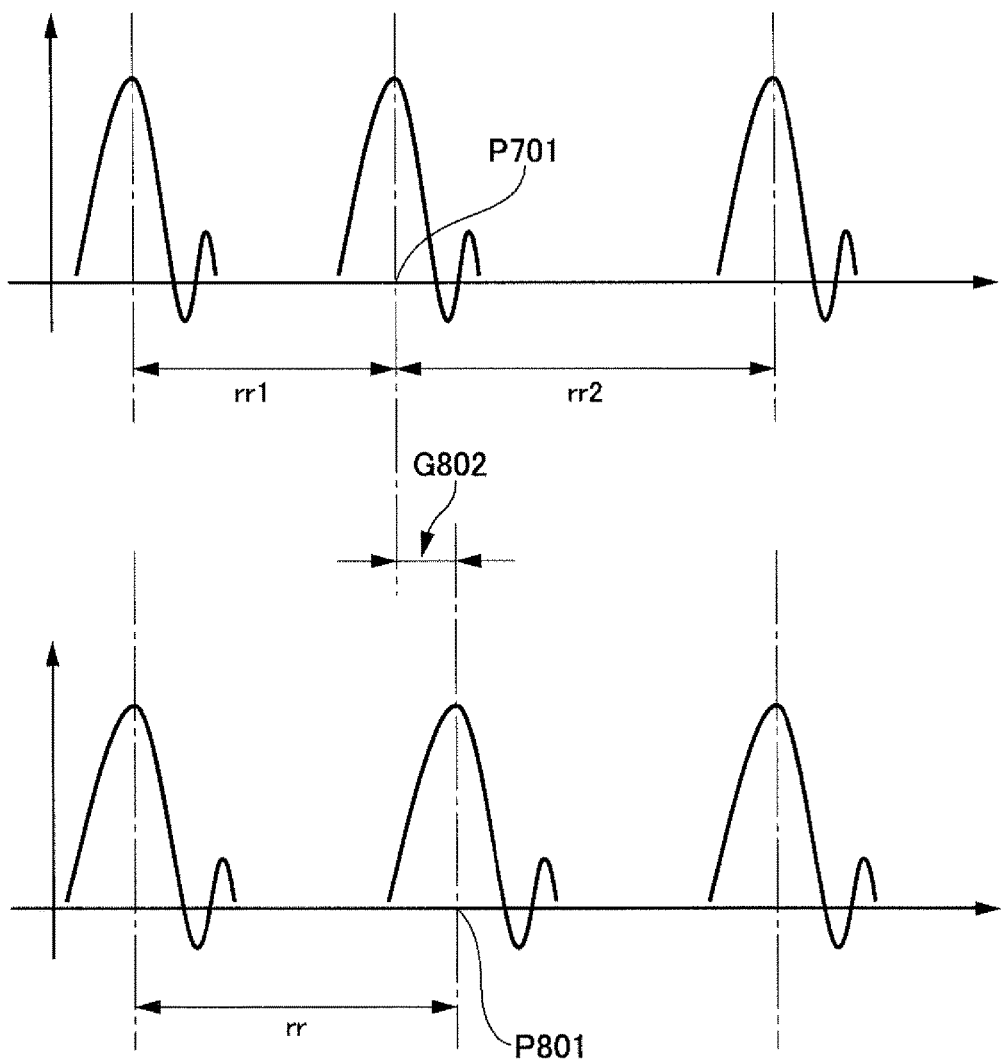
FIG. 8 shows a waveform diagram of a heartbeat waveform before being subjected to reposition processing and a waveform diagram of a heartbeat waveform after being subjected to the reposition processing.

FIG. 8 shows a waveform diagram of a heartbeat waveform before being subjected to the reposition processing and a waveform diagram of a heartbeat waveform after being subjected to the reposition processing. The data actually to be subjected to the reposition processing is the heart sound data; however, in order to facilitate understanding, the reposition processing is explained below using an example in which the processing of the reposition processing section 408 is performed on a heartbeat waveform.

It is known that the RR interval of a healthy person periodically increases and decreases repeatedly. In other words, the RR interval continuously varies, instead of being constantly unchanged. If an orthogonal transformation (such as a discrete Fourier transformation) is performed on the heart sound data as it is, it will be difficult to remove the noise components due to the periodic variation. To solve such problem, before inputting the heart sound data into the noise removal processing section 411 (which removes noise by performing an orthogonal transformation) provided in the subsequent stage, the waveform of the heart sound data is forcibly arranged at an equal interval.

As described above, the heartbeat detector 407 has detected the R-wave address information P701, and therefore the RR interval has been obtained. The reposition processing section 408 first extracts all RR intervals (i.e., the distances between the R-wave address information P701) detected from the heartbeat buffer 401, and calculates the average value of the extracted RR intervals. The average value is referred to as "RR average". Next, based on the RR average, the reposition processing section 408 rearranges the R-wave address information P701 detected by the heartbeat detector 407 at an interval equivalent to the RR average, and the result obtained is referred to as repositioned R-wave address information P801.

Further, the reposition processing section 408 cuts out the heart sound data in the heart sound buffer 403 based on the cut-out R-wave address information A702, moves the cut out heart sound data by an address moving amount G802, which represents a difference between the R-wave address information P701 and the repositioned R-wave address information P801, and stores the result in a reposition buffer 409. If simply cutting out the heart sound data, since noise occurs in edge portions of the cut out heart sound data, interpolation processing will be performed on the repositioned heart sound data in the reposition buffer 409 by an interpolation processing section 410 provided within the reposition processing section 408. Such interpolation processing can be achieved by using a known interpolation, such as a linear interpolation, a Lagrange interpolation, a spline interpolation or the like; particularly, a good arithmetic result can be obtained by the Lagrange interpolation.

Thus, the reposition processing section 408 outputs the repositioned heart sound data and the repositioned R-wave address information P801. The repositioned heart sound data is stored in the reposition buffer 409. The repositioned R-wave address information P801 is supplied to a position restoration processing section 413 (which will be described later), in which the repositioned R-wave address information P801, together with the R-wave address information P701 and the cut-out address information A702 outputted by the heartbeat detector 407, is used in processing for restoring the position of the heart sound waveform of the noise-removed repositioned heart sound data to its original position on the time axis.

The noise of the repositioned heart sound data stored in the reposition buffer 409 is removed by the noise removal processing section 411. The noise removal processing section 411 removes the noise by using an orthogonal transformation and an orthogonal inverse transformation. There are various known orthogonal transformation methods; among these methods, three typical orthogonal transformation methods will be used to describe the processing of removing the noise with reference to FIG. 5A, FIG. 5B and FIG. 5C.

FIG. 5A shows an example of a block diagram of software functions of a noise removal processing section 411 using a discrete cosine transformation.

The repositioned heart sound data (which is a discrete data row) stored in the reposition buffer 409 is converted into a coefficient data row by a DCT transformation processing section 501, wherein the coefficient data row has the same sample number as that of the discrete data row. A high-order coefficient data thinning processing is performed on the coefficient data row by a coefficient filter 502. The coefficient data row having been subjected to the high-order coefficient data thinning processing is converted into a decoded discrete data row by a DCT inverse transformation processing section 503, and stored in a processed buffer 412, wherein the decoded discrete data row has the same sample number as that of the discrete data row.

The decoded discrete data row becomes the noise-removed repositioned heart sound data.

FIG. 5B shows an example of a block diagram of software functions of a noise removal processing section 411 using a discrete Fourier transformation.

The repositioned heart sound data (which is a discrete data row) stored in the reposition buffer 409 is converted into a complex data row by a FFT transformation processing section 511, wherein the complex data row has the same sample number as that of the discrete data row. A real part data row and an imaginary part data row of the complex data row are converted into an amplitude data row and a frequency/phase data row by a vector operation processing section 512, wherein the amplitude data row and the frequency/phase data row each have the same sample number as that of the discrete data row. The amplitude data row has its high-frequency component eliminated by a high-pass filter (hereinafter referred to as "LPF") 513. The amplitude data row having its high-frequency components eliminated and the frequency/phase data row are converted into a complex data row by an inverse vector operation processing section 514. Further, the complex data row is converted into a decoded discrete data row by a FFT inverse transformation processing section 515, and the decoded discrete data row is stored in the processed buffer 412.

The decoded discrete data row becomes the noise-removed repositioned heart sound data.

Figure 5C:
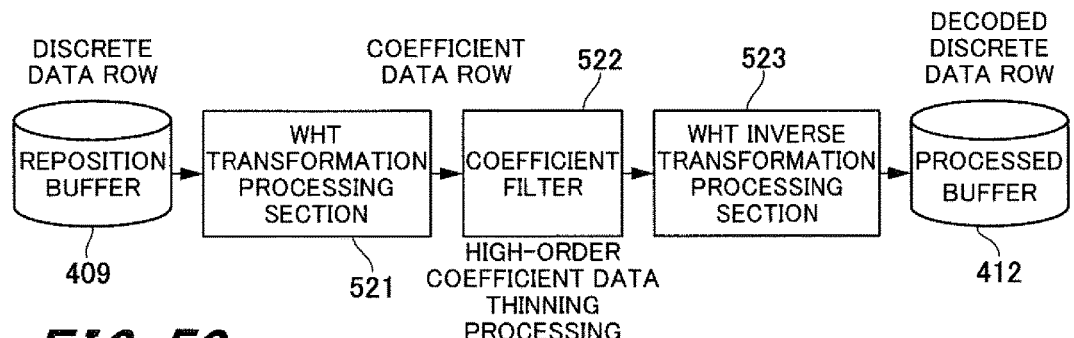

FIG. 5C shows an example of a block diagram of software functions of a noise removal processing section 411 using a discrete Walsh-Hadamard transformation.

The repositioned heart sound data (which is a discrete data row) stored in the reposition buffer 409 is converted into a coefficient data row by a WHT transformation processing section 521, wherein the coefficient data row has the same sample number as that of the discrete data row. A high-order coefficient data thinning processing is performed on the coefficient data row by a coefficient filter 522. The coefficient data row having been subjected to the high-order coefficient data thinning processing is converted into a decoded discrete data row by a WHT inverse transformation processing section 523, and stored in the processed buffer 412, wherein the decoded discrete data row has the same sample number as that of the discrete data row.

The decoded discrete data row becomes the noise-removed repositioned heart sound data.

If viewed on a functional block basis, it seems like that the noise removal processing performed by the discrete Walsh-Hadamard transformation shown in FIG. 5C has no any difference from the noise removal processing performed by the discrete cosine transformation shown in FIG. 5A. However, as widely known, discrete Walsh-Hadamard transformation can perform matrix operations of addition and subtraction, and therefore calculation volume is significantly reduced. Thus, the Walsh-Hadamard transformation can be implemented in a one-chip microcomputer, which consumes less power but has lower computing power.

By the position restoration processing section 413, the position of the heart sound waveform of the noise-removed repositioned heart sound data in the processed buffer 412 on the time axis is restored to its original position before being moved by the reposition processing section 408. In other words, a heart sound waveform is cut out from the noise-removed repositioned heart sound data in the processed buffer based on address information obtained by shifting the cut-out address information A702 based on the difference between the R-wave address information P701 and the repositioned R-wave address information P801. Further, position restoration is performed based on the difference between the R-wave address information P701 and the repositioned R-wave address information P801, and the result is outputted as the noise-removed heart sound data.

A heart sound includes a blood flow sound. The blood flow sound is caused by the friction between blood and the inner walls of blood vessels when the blood flows in the blood vessels. Accordingly, the heart sound has strong correlation with the heartbeat cycle.

Thus, if it is possible to only extract frequency components having strong correlation with the heartbeat cycle, it will be possible to remove the noise not associated with the heartbeat cycle.

However, since the heartbeat cycle includes fluctuations peculiar to living bodies, the heartbeat cycle is subtly not constant.

Thus, the heartbeat detector 407 is used to extract the R-wave address information P701 and the cut-out address information A702 from the heartbeat data. Next, the reposition processing section 408 calculates the average value of the RR interval based on the R-wave address information P701 to derive the repositioned R-wave address information P801. Further, the reposition processing section 408 forcibly fits the heart sound data synchronous with the heartbeat data to the average cycle of the heartbeat. The noise component not associated with the heartbeat cycle can be removed from the heart sound by fitting the cut out heart sound waveform at an equal interval, and then performing an orthogonal transformation and an orthogonal inverse transformation.

After having performed the orthogonal inverse transformation, the waveform cut out by the orthogonal inverse transformation is restored to the original heartbeat cycle based on the R-wave address information P701, the repositioned R-wave address information P801, and the cut-out address information A702. By performing the above processing, the noise can be removed from the heart sound.

As shown in FIG. 3A and FIG. 3B, the noise-removed heart sound data is inputted to the blood pressure calculator 303. The blood pressure calculator 303 refers to a table in the blood pressure calculator 303 to calculate the blood pressure from the amplitude of the noise-removed heart sound data.

Second Embodiment: Software Functions of Heartbeat Pulse Detector 901

When achieving the present invention, the inventor of the present invention noticed that, in some cases, erroneous pulse was included in the heartbeat peak data outputted by the heartbeat detector 407. When investigating the cause of the erroneous pulse, the inventor found that, if the T-wave has a high peak value due to individual difference of the subject 103, there will be a possibility that the T-wave may be erroneously detected as the R-wave. Thus, the following measures are taken for improving the R-wave detecting function of the heartbeat detector 407.

Figure 9:
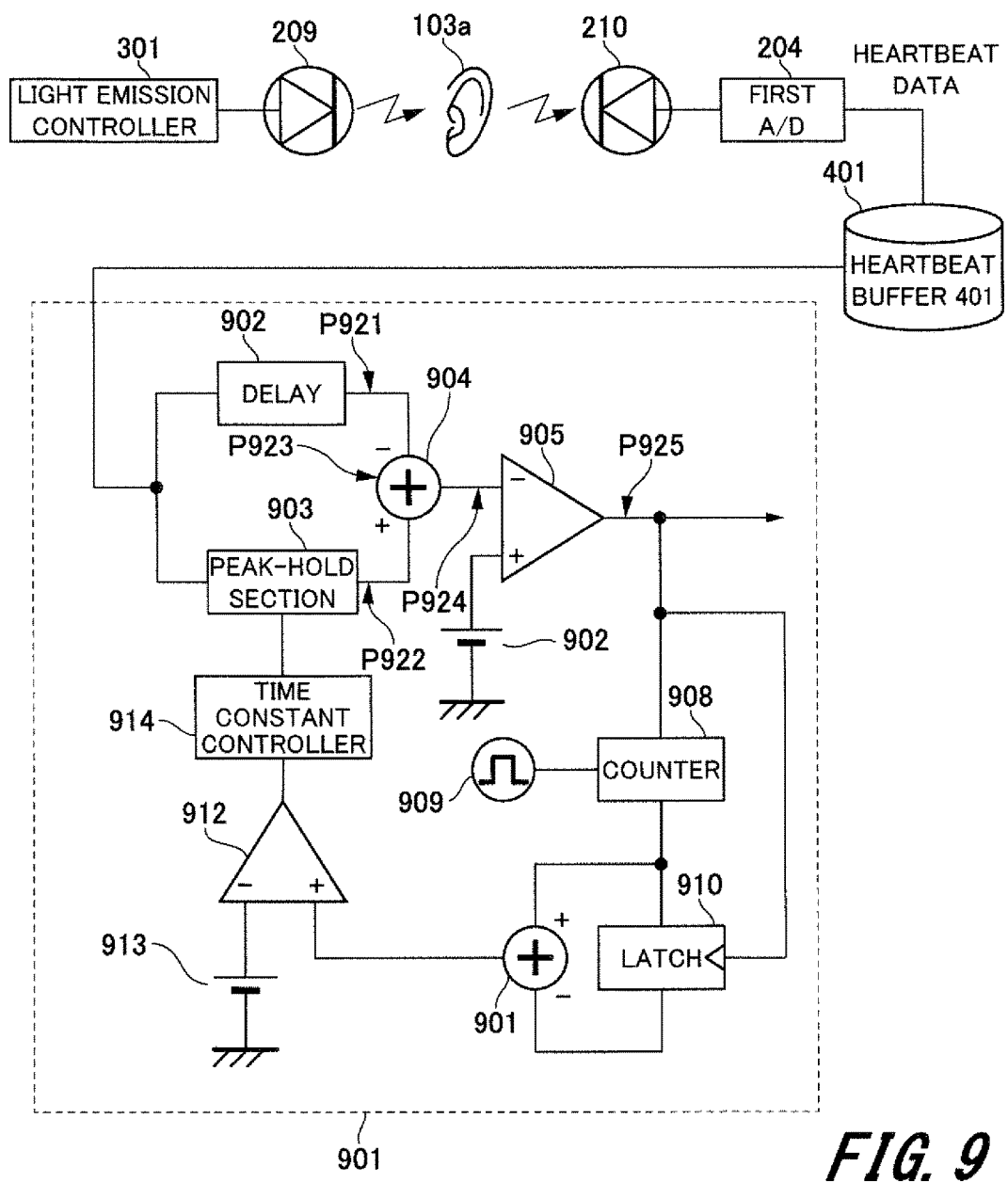
FIG. 9 is a block diagrams showing software functions of a heartbeat pulse detector, which is a function of a part of a heartbeat detector.

FIG. 9 is a block diagrams showing software functions of a heartbeat pulse detector 901, which is a function of a part of the heartbeat detector 407. Incidentally, the function of the heartbeat pulse detector 901 is achieved by software; however, in order to simplify the description, a pseudo analog circuit function is described in place of the software.

The heartbeat data outputted from the heartbeat buffer 401 (or from the first A/D converter 204) is supplied to a delay 902 and a peak-hold section 903. Similar to a widely known peak-hold circuit in an analog circuit, the peak-hold section 903 outputs a peak-hold signal that attenuates with a time constant. The delay 902 is adapted to provide a delay time to the input data so that the data is matched on the time axis in a subsequent first adder 904, wherein the delay time provided by the delay 902 is equal to the delay (the latency) caused due to the signal processing of the peak-hold section 903.

The first adder 904 subtracts the data of the delay 902 from the data of the peak-hold section 903. The data outputted from the first adder 904 is compared to a reference signal level value 907 by a first comparator 906; if the data outputted from the first adder 904 is equal to or smaller than the reference signal level value 907, the first comparator 906 will output a logical true. In such a manner, the first comparator 906 outputs a pulse equivalent to the R-wave of the heartbeat from the inputted data.

The output logic signal of the first comparator 906 is inputted to a counter 908. The counter 908 (which is also referred to as a "cycle measuring section") counts the interval between the output logic signals of the first comparator 906 with a system clock 909, and outputs the counted value.

The output logic signal of the first comparator 906 is also inputted to the reset terminal of a latch 910. The latch 910 stores the output data of the counter 908.

The output data of the counter 908 and the output data of the latch 910 are inputted to a second adder 911. The second adder 911 subtracts the output data of the latch 910 from the output data of the counter 908.

The output data of the second adder 911 is supplied to a second comparator 912. The second comparator 912 compares the output data of the second adder 911 with a reference differential value 913; if the output data of the second adder 911 is equal to or larger than the reference differential value 913, the second comparator 912 will output a logical true. In such a manner, when the differential value outputted by the second adder 911 becomes equal to or larger than the reference differential value 913, the second comparator 912 will provide a logical true to a subsequent time constant controller 914.

The time constant controller 914 is adapted to control the peak-hold section 903 so that when the output logical value of the second comparator 912 is a logical true, the peak-hold section 903 will be controlled to increase the time constant.

Second Embodiment: Operation of Heartbeat Pulse Detector 901

Figure 10:
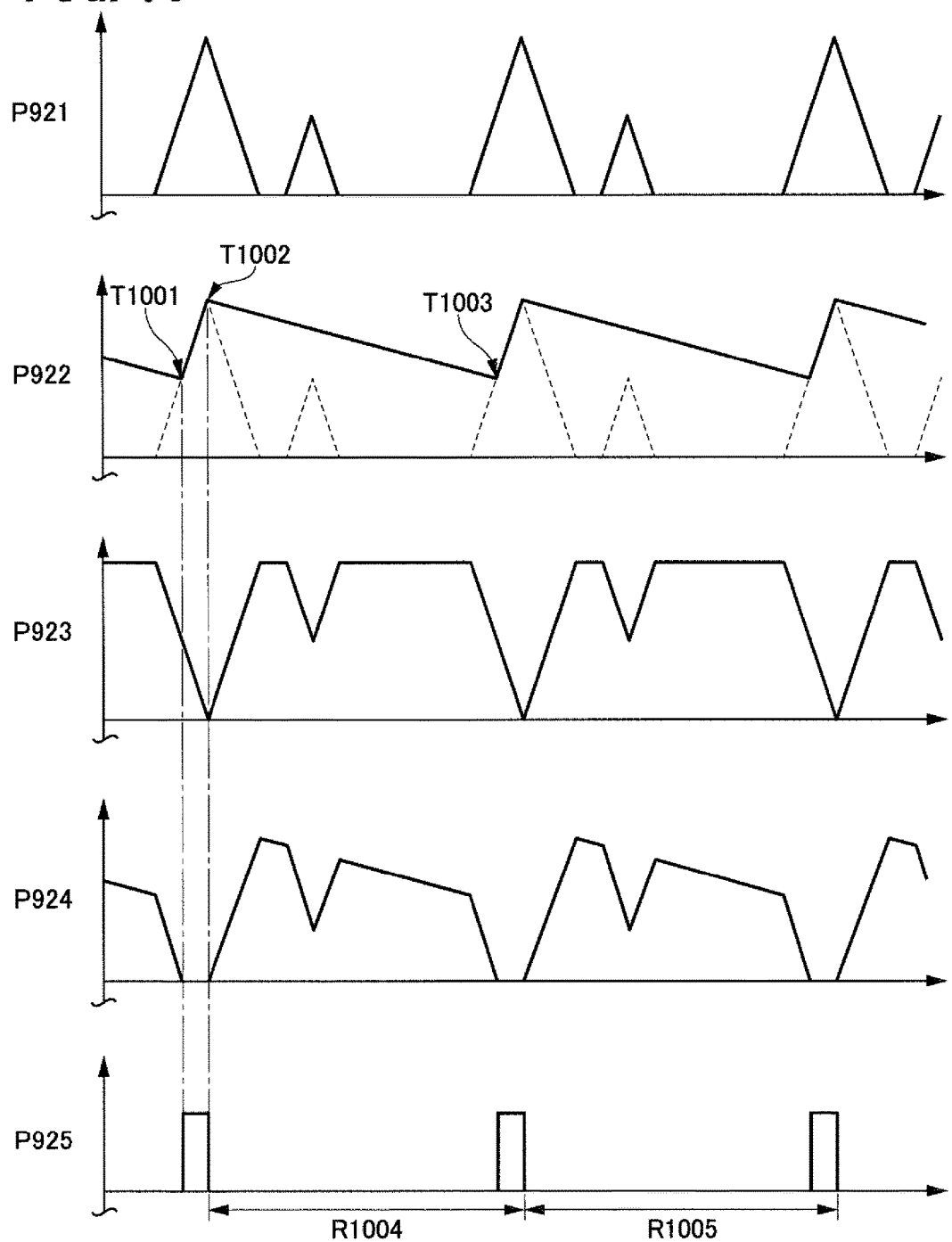
FIG. 10 schematically shows waveform diagrams of data at respective points of the heartbeat pulse detector, in a case where the heartbeat pulse detector has normally detected an R-wave.
Figure 11:
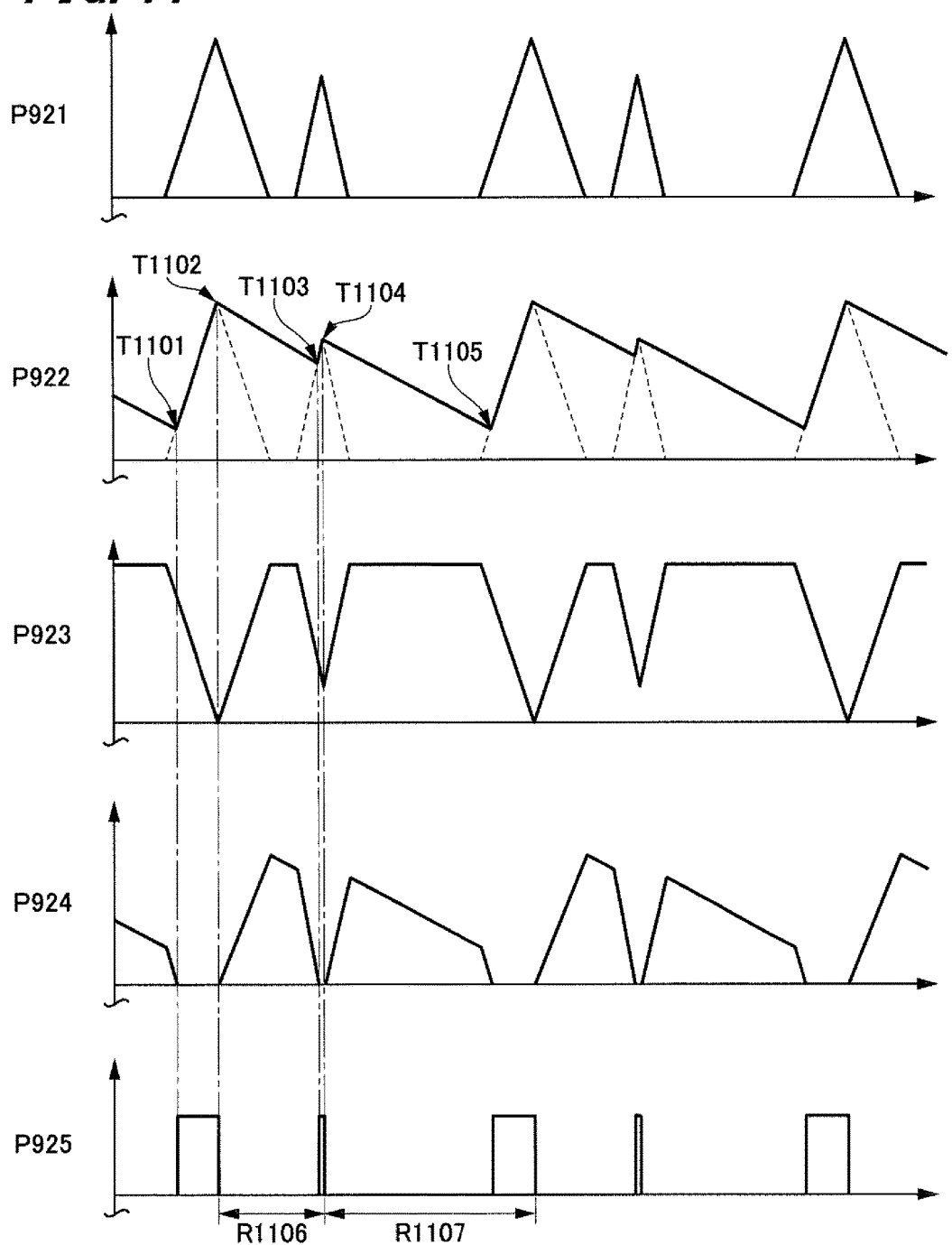
FIG. 11 schematically shows waveform diagrams of data at respective points of the heartbeat pulse detector, in a case where the heartbeat pulse detector has failed to detect the R-wave.

FIG. 10 schematically shows waveform diagrams of data at respective points of the heartbeat pulse detector 901, in a case where the heartbeat pulse detector 901 has normally detected the R-wave. FIG. 11 schematically shows waveform diagrams of data at respective points of the heartbeat pulse detector 901, in a case where the heartbeat pulse detector 901 has failed to detect the R-wave. To simplfy the description, in FIG. 10 and FIG. 11, only the R-wave and the T-wave of the heartbeat waveform are indicated, and it is assumed that the R-wave and the T-wave are to be triangular waves, and waveform components in negative direction are eliminated.

The waveform diagram at a measurement point P921 represents the heartbeat data whose time axis has been aligned with that of the output data of the peak-hold section 903 by the delay 902. On the other hand, the waveform diagram at a measurement point P922 represents the output data of the peak-hold section 903, i.e., the data of the waveform that attenuates with the time constant from the peak of the R-wave.

The waveform diagram at a measurement point P923 represents an inverse value of the heartbeat data at the measurement point P921.

The waveform diagram at a measurement point P924 represents the data outputted by the first adder 904.

The waveform diagram at a measurement point P925 represents the logical value outputted by the first comparator 906.

First, the operation of the heartbeat pulse detector 901 at normal time will be described below with reference to FIG. 10.

The peak-hold section 903 outputs the data that attenuates with the time constant from the time when the peak value has been obtained. Detection of peak is started at a time point when the attenuated data becomes smaller than the inputted data. Such time point is a time point T1001 in FIG. 10. Next, at a time point when the inputted data passes the peak so as to star to attenuate, the peak-hold section 903 outputs the data that attenuates with the time constant. Such time point is a time point T1002 in FIG. 10. Further, the data formed by the peak-hold section 903 is outputted until a time point when the attenuated data becomes smaller than the inputted data again. Such time point is a time point T1003.

In other words, the period between the time point T1001 and the time point T1002 is a state where the data inputted appears from the data formed by the peak-hold section 903. Conversely, the period between the time point T1002 and the time point T1003 is a state where the data outputted is hidden (masked) by the data formed by the peak-hold section 903.

When subtracting the inputted data from the data appears from the masking, if the absolute value of the data from the data appears from the masking is equal to the absolute value of the inputted data, the value of the absolute will become zero. Such period is a period between the time point T1001 and the time point T1002 at the measurement point P924. If the period between the time point T1001 and the time point T1002 is detected by the first comparator 906, it will be possible to detect the peak of the R-wave.

An interval R1004 and an interval R1005, each represents an RR interval detected by the peak of the R-wave detected in the above manner, are values close to each other. The difference between the interval R1004 and the interval R1005 is a small value based on the fluctuation of the heartbeat of the human.

Due to elements such as the offset included in the inputted data, the error of the reference signal level value 907 applied to the first comparator 906 and the like, the error caused when the first comparator 906 captures the time point T1001 and the time point T1002 actually does not cause any problem in actual use.

Based on the above description, the operation of the heartbeat pulse detector 901 at abnormal time will be described below with reference to FIG. 11.

In FIG. 11, a time point T1101 is identical to the time point T1001 of FIG. 10. Similarly, a time point T1102 is identical to the time point T1002, and a time point T1105 is identical to the time point T1003 of FIG. 10.

When the peak value of the T-wave is large to a level close to the R-wave, and/or when the time constant of the peak-hold section 903 is small, the T-wave will also appear from masking. Such period is a period between the time point T1103 and the time point T1104 in FIG. 11. As a result, the T-wave, which is supposed not to be detected, is also outputted from the first comparator 906 due to being erroneously detected as the R-wave.

An interval R1106 and an interval R1107, each is an RR interval detected by the peak of the R-wave detected in the above manner, are values largely different from each other.

Thus, whether or not the detection of the R-wave is normal can be determined by comparing the current RR interval with the last RR interval. Such function is achieved by the counter 908, the latch 910, the second adder 911 and the second comparator 912.

It will be ideal if the time constant of the peak-hold section 903 is constantly an optimal value; however, it is difficult to figure out such value. To solve such a problem, in the heartbeat pulse detector 901 of the present embodiment, the time constant of the peak-hold section 903 is adaptively controlled. To be specific, when it is determined that the detection of the R-wave is in abnormal state, the time constant of the peak-hold section 903 will be increased; and that is the function of the time constant controller 914.

Third Embodiment: Overall Configuration of Biological Signal Detecting Device

The blood pressure measuring system 101 has been disclosed in the first embodiment. By providing a heart sound signal and a heartbeat signal to the blood pressure measuring system 101 of the first embodiment, it is possible to remove the noise from the heart sound signal, and calculate the blood pressure. In the blood pressure measuring system 101, the heart sound signal is detected by an acoustic microphone, and the heartbeat signal is detected by a photoelectric sensor formed by the LED 209 and the photodiode 210. These sensors need to be brought into contact with the human body. If these sensors can be uses in a non-contact manner, it will be possible to achieve an in-vehicle blood pressure measuring system 1201 to be incorporated into a vehicle or the like.

Figure 12:
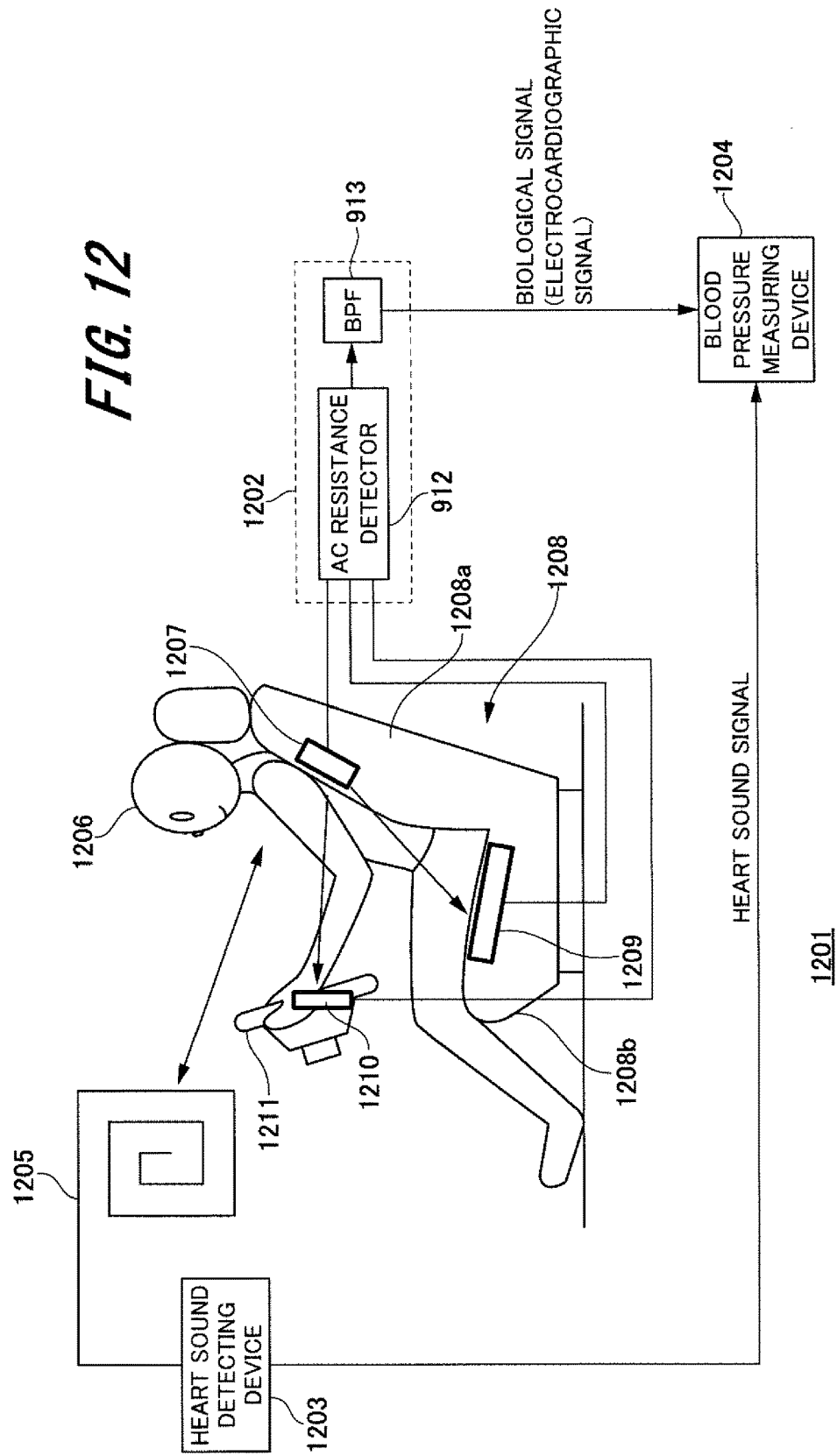
FIG. 12 is a schematic view showing an overall configuration of an in-vehicle blood pressure measuring system.

FIG. 12 is a schematic view showing an overall configuration of the in-vehicle blood pressure measuring system 1201.

The in-vehicle blood pressure measuring system 1201 includes a biological signal detecting device 1202, a heart sound detecting device 1203, and a blood pressure measuring device 1204. Among these components, the blood pressure measuring device 1204 is equivalent to the signal processing section 302 and blood pressure calculator 303 of the blood pressure measuring system 101.

The heart sound detecting device 1203 irradiates a weak radio wave with a frequency of about 60 MHz emitted from a helical antenna 1205 to a driver 1206, and detects the heart sound signal from the reflected wave reflected by the driver 1206.

The biological signal detecting device 1202 has three antennas connected thereto, which are a first antenna 1207, a second antenna 1209, and a third antenna 1210.

The first antenna 1207 is a square-shaped metal plate whose side length is about 5 to 10 cm, and is embedded in a backrest 1208a of a driver seat 1208.

Similar to the first antenna 1209, the second antenna 1207 is also a square-shaped metal plate whose side length is about 5 to 20 cm, and is embedded in a seat 1208b of the driver seat 1208.

The third antenna 1210 is a metal wire embedded in a steering 1211 of the vehicle. Alternatively, the third antenna 1210 may also be embedded in a dashboard provided near the steering 1211, instead of being embedded in the steering 1211. At this time, the third antenna 1210 is formed in the same shape as that of the first antenna 1207 and the second antenna 1209, i.e., formed as a square-shaped metal plate whose side length is about 5 to 10 cm.

An AC resistance detector 1212 of the biological signal detecting device 1202 emits a weak unmodulated radio wave from the first antenna 1207, wherein the unmodulated radio wave has a HF band ranging from several MHz to several tens of MHz. The radio wave is received from the second antenna 1209 and the third antenna 1210. Since the AC resistance detector 1212 outputs a signal containing the biological signals, a band-pass filter (hereinafter referred to as "BPF") 1213 removes a DC offset component and a high-frequency noise component, and outputs a biological signal substantially equivalent to an electrocardiographic signal.

Thus, the biological signal obtained from the biological signal detecting device 1202 and the heart sound signal obtained from the heart sound detecting device 1203 are inputted to the blood pressure measuring device 1204, and the blood pressure of the subject 103 is measured.

Figure 13:
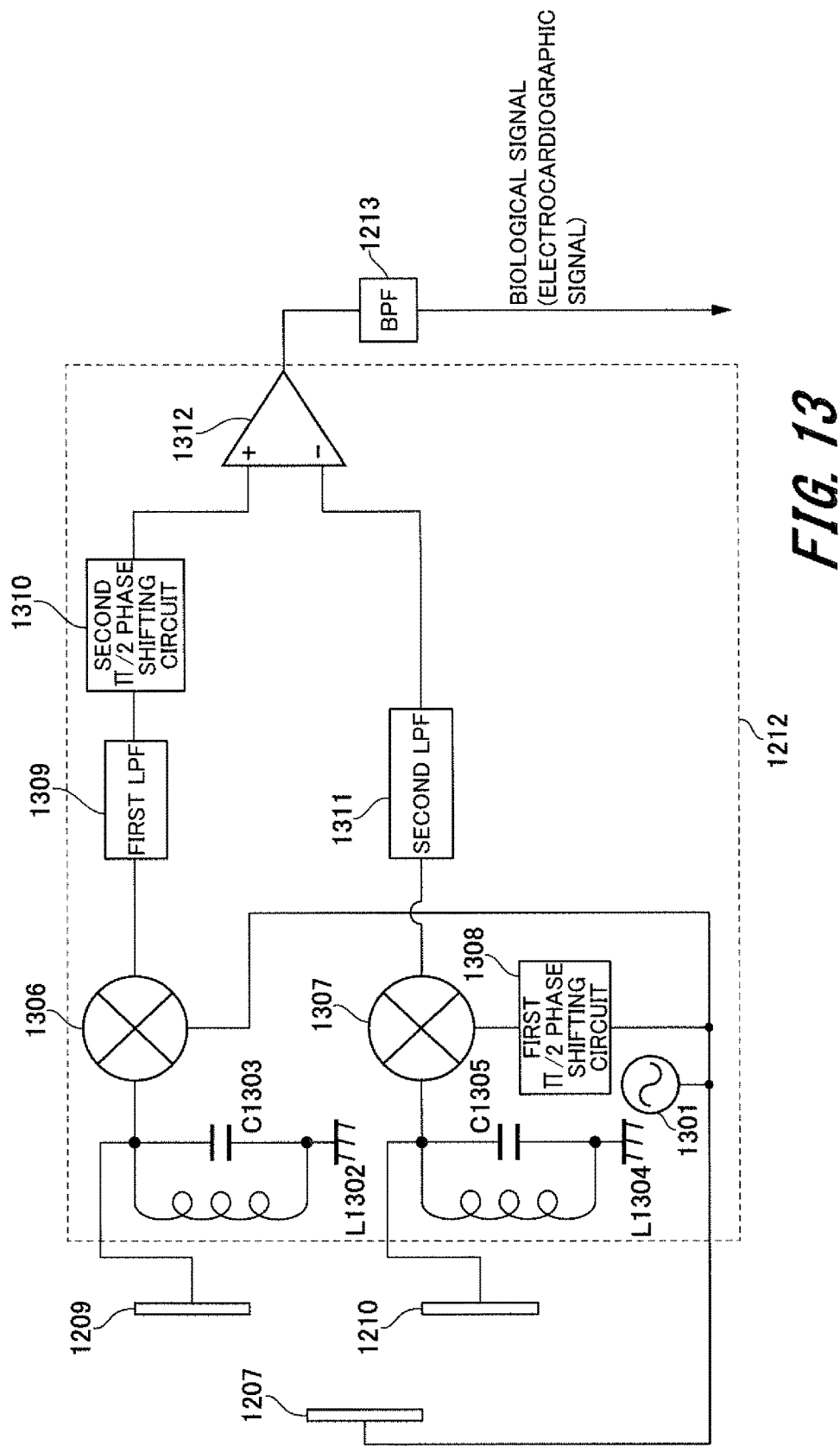
FIG. 13 is a functional block diagram of a biological signal detecting device.

FIG. 13 is a functional block diagram of the biological signal detecting device 1202.

An oscillation source 1301 generates an unmodulated high-frequency signal having a HF band ranging from several MHz to several tens of MHz. The unmodulated high-frequency signal is transmitted from the first antenna 1207 as an unmodulated radio wave.

The second antenna 1209 has a tuned circuit connected thereto, wherein the tuned circuit includes a coil L1302 and a capacitor C1303. The third antenna 1210 also has a tuned circuit connected thereto, wherein the tuned circuit includes a coil L1304 and a capacitor C1305.

The output signal of the tuned circuit connected to the second antenna 1209 is applied to a first mixer 1306. The unmodulated high-frequency signal of the oscillation source 1301 is also inputted to the first mixer 1306.

The output signal of the tuned circuit connected to the third antenna 1210 is applied to a second mixer 1307. The unmodulated high-frequency signal of the oscillation source 1301 is inputted to the second mixer 1307 through a first $\pi/2$ phase shifting circuit 1308. In other words, a signal obtained by delaying the unmodulated high-frequency signal of the oscillation source 1301 by π/2 phase is inputted to the second mixer 1307. Incidentally, a dual gate FET, for example, can be used as the first mixer 1306 and the second mixer 1307.

The output signal of the tuned circuit connected to the second antenna 1209 and the unmodulated high-frequency signal of the oscillation source 1301 are supplied to the first mixer 1306, a sum signal and a difference signal of these frequency components are supplied to a first LPF 1309 as the output signal of the first mixer 1306. Of the inputted sum signal and difference signal of the frequency components, the first LPF 1309 only outputs the difference signal. Further, the output signal of the first LPF 1309 is delayed by a second π/2 phase shifting circuit 1310 by π/2 phase.

The output signal of the tuned circuit connected to the third antenna 1210 and the signal obtained by delaying the unmodulated high-frequency signal of the oscillation source 1301 by π/2 phase are supplied to the second mixer 1307, and a sum signal and a difference signal of these frequency components are supplied to a second LPF 1311 as the output signal of the second mixer 1307. Of the inputted sum signal and difference signal of the frequency components, the second LPF 1311 only outputs the difference signal.

The output signal of the second π/2 phase shifting circuit 1310 and the output signal of the second LPF 1311 are inputted to a differential amplifier 1312. The differential amplifier 1312 cancels out the same in-phase components of the output signal of the second π/2 phase shifting circuit 1310 and the output signal of the second LPF 1311, and only outputs the reverse-phase components of the both output signals. Further, the output signal of the differential amplifier 1312 is inputted to the BPF 1213.

Except for the two tuned circuits, the first mixer 1306, the second mixer 1307, the first π/2 phase shifting circuit 1308, the first LPF 1309, the second π/2 phase shifting circuit 1310, and the second LPF 1311 are identical to those of a known synchronous detection circuit.

The heartbeat (i.e., change in pressure of blood flow) results in a phenomenon of so-called "variation in impedance of the human body". A biological signal substantially equal to the heartbeat signal is detected by connecting electrodes to a plurality of points of the human body, supplying a weak AC signal to the electrodes, and detecting variation in impedance of the human body. The biological signal detecting device 1202 according to the present embodiment uses a radio wave to detect the variation in impedance of the human body in a non-contact manner.

However, when propagating a radio wave from a transmission side to a reception side with an object interposed therebetween, the gain of the detection signal on the reception side will largely fluctuate depending on the object interposed between the transmission side and the reception side. In the case shown in FIG. 12, the signal level on the reception side will largely fluctuate if the driver 1206 (i.e., the subject) moves even slightly.

To solve such problem, a synchronous detection circuit is used in the biological signal detecting device 1202 of the present embodiment. By providing two antennas and two tuned circuits on the reception side, the fluctuation of the signal level based on the movement of the human body is cancelled out as the in-phase components by the differential amplifier 1312, and the fluctuation of the signal level based on the variation in impedance of the human body is detected as the reverse-phase components by the differential amplifier 1312. In other words, the variation in impedance of the human body is equivalent to generating an amplitude modulation with respect to the unmodulated high-frequency signal.

Figure 14:
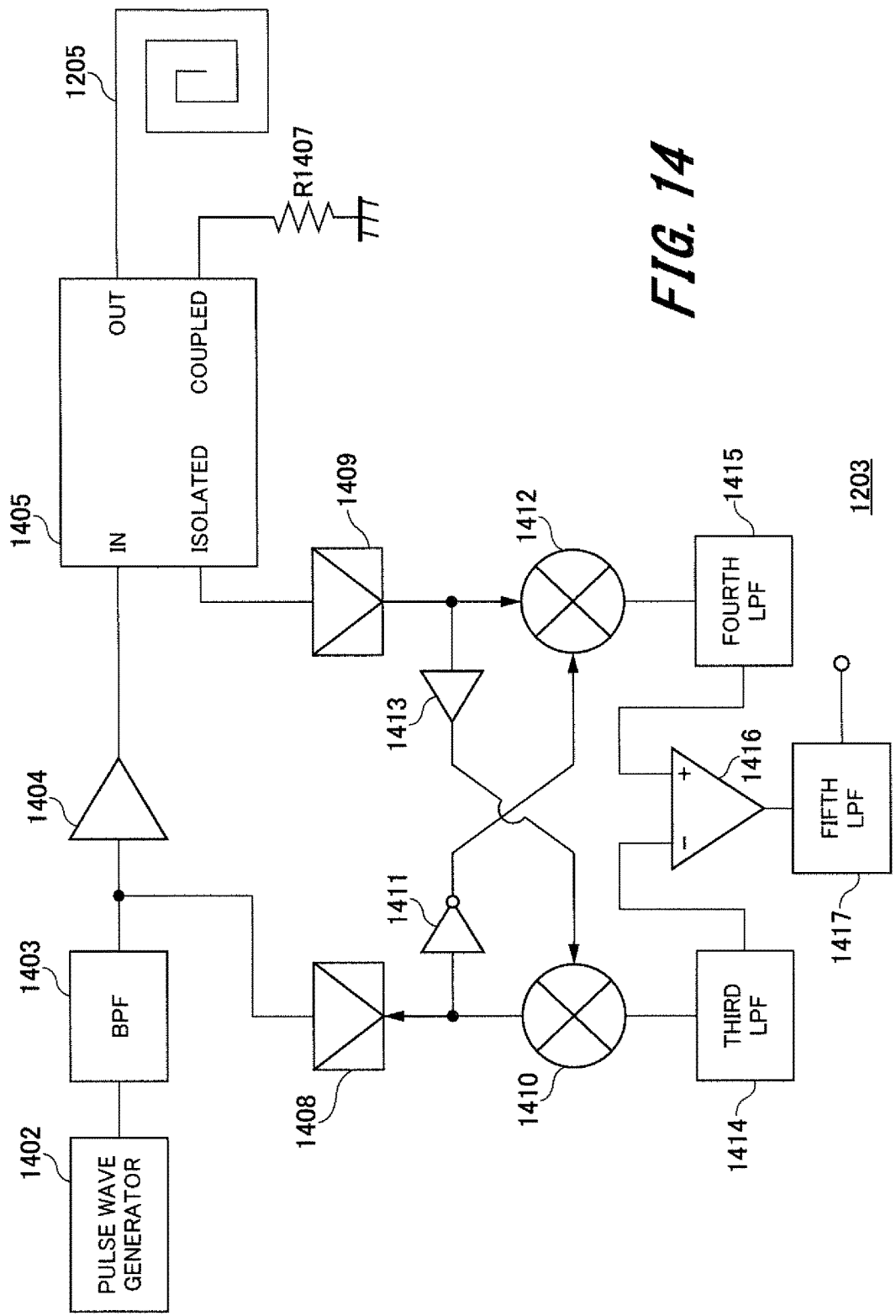
FIG. 14 is a functional block diagram of a heart sound detecting device.

FIG. 14 is a functional block diagram of the heart sound detecting device 1203. The technical content of the heart sound detecting device 1203 is disclosed in a patent application for a "pulse sensor" (JP2013-217093) which is filed by the inventor of the present application.

The heart sound detecting device 1203 can be divided into the following two elements.

The first element is transmitting a radio wave (which is a traveling wave) to an object, and receiving and extracting a reflected wave reflected from the object. The first element includes a pulse wave generator 1402, a BPF 1403, a first RF amplifier 1404, a directional coupler 1405, and the aforesaid helical antenna 1205 (as a fourth antenna).

The second element is generating a frequency difference signal from the traveling wave and the reflected wave, and extracting a signal of the pulse. The second element includes a second RF amplifier 1408, a third RF amplifier 1409, a third mixer 1410, a fourth mixer 1412, a third LPF 1414, a fourth LPF 1415, a differential amplifier 1416, and a fifth LPF 1417.

The pulse wave generator 1402 (which may also be referred to as a "signal generator") generates a pulse having relatively low frequency. The frequency of the pulse generated by the pulse wave generator 1402 is, for example, 1 MHz.

The BPF 1403 extracts harmonic components from the pulse generated by the pulse wave generator 1402. The central frequency and bandwidth of the BPF 1403 is, for example, 60 MHz±3 MHz. For example, a circuit structure obtained by connecting multiple stages of LC resonance circuits can be used as the BPF 1403.

The first RF amplifier 1404 amplifies the signal of the harmonic components passed through the BPF 1403.

The signal of the harmonic components having been amplified by the first RF amplifier 1404 is inputted to an input terminal of the directional coupler 1405 (the terminal indicated as "IN" in FIG. 14). Further, the signal of the harmonic components is supplied to the helical antenna 1205 connected to an output terminal of the directional coupler 1405 (the terminal indicated as "OUT" in FIG. 14).

The directional coupler 1405 is a widely known circuit element configured by a coil(s), a capacitor(s), and a resistor(s), and is used in a VSWR (Voltage Standing Wave Ratio) meter or the like. The directional coupler 1405 can respectively output an output signal proportional to the traveling wave and an output signal proportional to the reflected wave based on the traveling wave and the reflected wave included in a first transmission path.

The helical antenna 1205 emits a radio wave having a plurality of frequencies based on the signal of the harmonic components. Further, the radio wave reflected by the object (such as a human body) is received by the helical antenna 1205 to generate a standing wave in the directional coupler 1405.

A signal proportional to the signal of the radio wave inputted from the output terminal of the directional coupler 1405 through the helical antenna 1205 (i.e., the reflected wave) is outputted to an insulated terminal of the directional coupler 1405 (the terminal indicated as "INSULATED" in FIG. 14).

A signal proportional to the signal of the harmonic components (i.e., the traveling wave) inputted to the input terminal of the directional coupler 1405 is outputted to a coupled terminal of the directional coupler 1405 (the terminal indicated as "COUPLED" in FIG. 14).

The coupled terminal is connected to a ground node through a resistor R1407. The resistance of the resistor R1407 is set to a value equal to the impedance of the directional coupler 1405 or helical antenna 1205. In most cases, the value of the resistor R1407 is set to 50Ω or 75Ω.

The second RF amplifier 1408 amplifies the signal of the harmonic components passed through the BPF 1403 (i.e., the traveling wave).

The third RF amplifier 1409 amplifies the signal of the radio wave (i.e., the reflected wave) inputted from the output terminal through the helical antenna 1205 and outputted from the insulated terminal of the directional coupler 1405.

The output signal of the second RF amplifier 1408 is supplied to the fourth mixer 1412 through an inverting amplifier 1411, as well as being supplied to the third mixer 1410.

The output signal of the third RF amplifier 1409 is supplied to the third mixer 1410 through a buffer 1413, as well as being supplied to the fourth mixer 1412. Incidentally, even if the phase of the output signal of the second RF amplifier 1408 and the phase of the output signal of the third RF amplifier 1409 are different from each other, a desired signal can be obtained from the third mixer 1410 and the fourth mixer 1412. Thus, a buffer (a non-inverting amplifier) can be used instead of the inverting amplifier 1411.

Thus, the third mixer 1410 and the fourth mixer 1412 each output a multiplication signal of the traveling wave and the reflected wave. Here, a dual gate FET, for example, can be used as the third mixer 1410 and the fourth mixer 1412.

The output signal of the third mixer 1410 is supplied to the third LPF 1414. Of the multiplication signal of the traveling wave and the multiplication signal of the reflected wave outputted from the third mixer 1410, the third LPF 1414 outputs a difference signal between the frequency of the traveling wave and the frequency of the reflected wave.

Similarly, the output signal of the fourth mixer 1412 is supplied to the fourth LPF 1415. Of the multiplication signal of the traveling wave and the multiplication signal of the reflected wave outputted from the fourth mixer 1412, the fourth LPF 1415 outputs a difference signal between the frequency of the traveling wave and the frequency of the reflected wave.

The output signal of the third LPF 1414 and the output signal of the fourth LPF 1415 are inputted to the differential amplifier 1416. The differential amplifier 1416 (which is an operational amplifier) outputs a signal obtained by removing noise components from both the output signal of the third LPF 1414 and the output signal of the fourth LPF 1415.

The output signal of the differential amplifier 1416 is supplied to the fifth LPF 1417. The fifth LPF 1417 removes AC components having relatively high frequency from the output signal of the differential amplifier 1416, and passes through a low frequency signal indicating the heart sound of the human body.

As described above, it is possible to achieve the blood pressure measuring system 101 capable of continuously measuring the blood pressure of a human body in a non-contact manner by supplying the heartbeat signal outputted by the biological signal detecting device 1202 and the heart sound signal outputted by the heart sound detecting device 1203 described in the present embodiment to the blood pressure measuring device 1204 based on the technical content described in the first embodiment.

The embodiments described above include the following applications.

(1) In the biological signal detecting device 1202 shown in FIG. 13, the second π/2 phase shifting circuit 1310 may also be connected to the subsequent stage of the second LPF 1311, instead of being connected to the subsequent stage of the first LPF 1309. At this time, the output signal of the first LPF 1309 is "USB+LSB" (wherein USB means "Upper Side Band", and LSB means "Lower Side Band") in the synchronous detection circuit, and the output signal of the second π/2 phase shifting circuit 1310 connected to the subsequent stage of the second LPF 1311 is "USB−LSB". The differential amplifier 1312 outputs the signal of USB.

(2) The blood pressure measuring system 101 of the first embodiment and the in-vehicle blood pressure measuring system 1201 of the third embodiment have the same configuration in the following components:

the biological signal detecting device 1202 that outputs the heartbeat signal of the subject 103;

the heart sound detecting device 1203 that outputs the heart sound signal of the subject 103; and the blood pressure measuring device 1204 that measures the blood pressure of the subject 103 using the heartbeat signal outputted from the biological signal detecting device 1202 and the heart sound signal outputted from the heart sound detecting device 1203.

The biological signal detecting device 1202 of the first embodiment is the heartbeat sensor 104 attached to the outer ear 103*a* of the subject 103.

The heart sound detecting device 1203 of the first embodiment is the heart sound microphone 105 attached to the chest of the subject 103.

(3) The blood pressure measuring method disclosed in Patent document 1 is based on a technique in which a table that includes data indicating the correspondence relation between the amplitude of the heart sound and the blood pressure is created based on a fact that the amplitude of the heart sound has correlation with the blood pressure, and the amplitude of the heart sound is converted into blood pressure data by referring to such table. By using such technical content, it is possible to prepare a table that includes data indicating the correspondence relation between the frequency of a signal constituting the heart sound, instead of the amplitude of the heart sound, and the blood pressure, and convert the frequency component of the heart sound into the blood pressure data. In such case, since the conversion from the frequency component of the heart sound to the blood pressure data is achieved by extracting information associated with the frequency of the signal constituting the heart sound from the inside of the noise removal processing section 411, the DCT inverse transformation processing section 503 shown in FIG. 5A (or the FFT inverse transformation processing section 515 shown in FIG. 5B, or the WHT inverse transformation processing section 523 shown in FIG. 5C) and the position restoration processing section 413 shown in FIG. 4 can be eliminated.

(4) The heartbeat pulse detector 901 of the second embodiment can be implemented alone as the heartbeat detecting device. It is possible to easily incorporate the heartbeat pulse detector 901 into various devices or applications which handle heartbeat signal.

In the present embodiment, the blood pressure measuring system has been described.

In the blood pressure measuring system 101 of the first embodiment, particularly the signal processing section 302, which can remove the noises mixed into the heart sound signal by using the heart sound signal and the heartbeat signal, has been described. The signal processing device 306 detects the R-wave of the heartbeat signal accompanied by periodic fluctuation to obtain the average value of the RR interval. Further, the waveform of the heart sound signal, which periodically fluctuates in synchronization with the heartbeat signal, is forcibly repositioned at an interval equivalent to the average value of the RR interval. After performing the reposition processing, the noise is removed by using the orthogonal transformation and the orthogonal inverse transformation, and the position of the obtained waveform is restored to its original position. As described above, it is possible to effectively remove the noise components not associated with the heartbeat cycle by performing the reposition processing before and after the noise removing processing.

In the heartbeat pulse detector 901 of the second embodiment, the possibility of the false detection of the R-wave can be reduced as far as possible by adaptively controlling the time constant of the peak-hold section 903, which functions in detecting the R-wave of the heartbeat signal. This technology contributes not only to the blood pressure measuring system disclosed in the specification of the present patent application, but also to improving the reliability of all equipment for detecting heartbeat.

In the in-vehicle blood pressure measuring system 1201 of the third embodiment, the biological signal detecting device 1202, which detects the heartbeat signal of the subject in a non-contact manner by using a radio wave, has been described. The radio wave transmitted from the oscillation source 1301 through the first antenna 1207 is received each by the second antenna 1209 and the third antenna 1210, and a synchronous detection is performed. The variation in impedance of the subject, i.e., the variation in impedance of the human body, causes an effect equivalent to performing amplitude modulation with respect to the unmodulated radio wave, and the gain fluctuation of a received radio wave caused due to the existence of the human body is cancelled out by the differential amplifier 1312. Thus, it is possible to detect the heartbeat signal of the subject in a non-contact manner by using synchronous detection.

The embodiments of the present invention are described as above; however, it is to be understood that the present invention is not limited to the embodiments described above, and various modifications and applications can be made without departing from the spirit described in the claims of the present invention.

For example, in the aforesaid embodiments, the configurations of the device and system are described in detail and concrete manner so that the present invention is easily understandable; however, the aforesaid configurations do not have to be fully included. Further, configurations of one embodiment can be partly substituted with configurations of another embodiment, and configurations of one embodiment can be added to a configuration(s) of another embodiment. Further, configurations of one embodiment can be partly omitted, or added with other configuration(s), or substituted with other configurations.

Further, the aforesaid each configuration, function, processor and the like can be partly or entirely achieved by hardware by being designed using an integrated circuit, for example. Further, the aforesaid each configuration, function and the like can be achieved by software whose processor explains and executes a program that achieves respective functions. Information such as the program, tables, files and the like for achieving each function can be stored in a volatile or non-volatile storage, such as a memory, a hard disk, a SSD (solid state drive) or the like, or a recording medium, such as an IC card, an optical disk or the like.

Further, a control line and an information line are shown because it is required for description, but the product does not necessarily show the control line and information line. It can be considered that almost all configurations are actually connected with each other.

REFERENCE SIGNS LIST

101 blood pressure measuring system
102 sensor driving device
103 subject
104 heartbeat sensor
105 heart sound microphone
106 information processing device
201 CPU
202 ROM
203 RAM
204 first A/D converter
205 second A/D converter
206 first buffer
207 second buffer
208 bus
209 LED
210 photodiode
213 first operational amplifier
214 second operational amplifier
215 short-range wireless communication section
221 CPU
222 ROM
223 RAM
224 nonvolatile storage
225 display
226 operating section
227 short-range wireless communication section
228 bus
229 touch panel display
301 light emission controller
302 signal processing section
303 blood pressure calculator
304 input/output controller
306 signal processing device
401 heartbeat buffer
402 delay
403 heart sound buffer
407 heartbeat detector
408 reposition processing section
409 reposition buffer
410 interpolation processing section
411 noise removal processing section
412 processed buffer
413 position restoration processing section
501 DCT transformation processing section
502 coefficient filter
503 DCT inverse transformation processing section
511 FFT transformation processing section
512 vector operation processing section
513 high-pass filter
514 inverse vector operation processing section
515 FFT inverse transformation processing section
521 WHT transformation processing section
522 coefficient filter
523 WHT inverse transformation processing section
901 heartbeat pulse detector
902 delay
903 peak-hold section
904 first adder
906 first comparator 907 reference signal level value
908 counter
909 system clock
910 latch
911 second adder
912 second comparator
913 reference differential value
914 time constant controller
1201 in-vehicle blood pressure measuring system
1202 biological signal detecting device
1203 heart sound detecting device
1204 blood pressure measuring device
1205 helical antenna
1206 driver
1207 first antenna
1208 driver seat
1209 second antenna
1210 third antenna
1211 steering
1212 AC resistance detector
1213 BPF
1301 oscillation source
1306 first mixer
1307 second mixer
1308 first π/2 phase shifting circuit
1309 first LPF
1310 second π/2 phase shifting circuit
1311 second LPF
1312 differential amplifier
1402 pulse wave generator
1403 BPF
1404 first RF amplifier
1405 directional coupler
1408 second RF amplifier
1409 third RF amplifier
1410 thirs mixer
1411 inverting amplifier
1412 fourth mixer
1413 buffer
1414 third LPF
1415 fourth LPF
1416 differential amplifier
1417 fifth LPF

The invention claimed is:

1. A heartbeat detecting device comprising:
a peak-hold section that holds the peak of a heartbeat signal;
a first adder that outputs a difference signal between an output signal of the peak-hold section and the heartbeat signal;
a first comparator that compares the output signal of the first adder with a predetermined reference signal level value;
a cycle measuring section that measures the cycle of the output signal of the first comparator;
a second adder that outputs the difference between the cycle measurement outputted by the cycle measuring section and the cycle measurement outputted last time by the cycle measuring section;
a second comparator that compares the value outputted by the second adder with a predetermined reference differential value; and
a time constant controller that controls an attenuation time constant of the peak-hold section according to a logical value of the second comparator.

2. The heartbeat detecting device according to claim 1, further comprising:
a delay that causes a delay equivalent to a latency of the peak-hold section, with respect to the heartbeat signal to be supplied to the first adder.

3. A biological signal processing device comprising:
a heartbeat buffer in which heartbeat data is stored, wherein the heartbeat data represents data of a heartbeat signal outputted by a biological signal detecting device that outputs the heartbeat signal of a subject;
a heart sound buffer in which heart sound data is stored, wherein the heart sound data represents data of a heart sound signal outputted from a heart sound detecting device that outputs the heart sound signal of the subject;
a heartbeat detector that outputs R-wave address information and cut-out address information from the heartbeat data, wherein the R-wave address information indicates the address of an R-wave of a heartbeat waveform, and the cut-out address information indicates the range of the heartbeat waveform;
a reposition processing section that cuts out a desired data portion from the heart sound data based on the R-wave address information and the cut-out address information, calculates an RR average, which represents the average value of RR intervals, from the heart sound data stored in the heart sound buffer and the R-wave address information, and repositions the data portion to form repositioned heart sound data;
a noise removal processing section that uses an orthogonal transformation and an orthogonal inverse transformation to remove noise components from the repositioned heart sound data to form noise-removed repositioned heart sound data; and
a position restoration processing section that uses the R-wave address information and the cut-out address information to resore the position of the noise-removed repositioned heart sound data on the time axis to the state of the heart sound data in the heart sound buffer,
wherein the heartbeat detector comprises:
a peak-hold section that holds the peak of a heartbeat signal;
a first adder that outputs a difference signal between an output signal of the peak-hold section and the heartbeat signal;
a first comparator that compares the output signal of the first adder with a predetermined reference signal level value;
a cycle measuring section that measures the cycle of the output signal of the first comparator;
a second adder that outputs the difference between the cycle measurement outputted by the cycle measuring section and the cycle measurement outputted last time by the cycle measuring section;
a second comparator that compares the value outputted by the second adder with a predetermined reference differential value; and
a time constant controller that controls an attenuation time constant of the peak-hold section according to a logical value of the second comparator.

* * * * *